(12) United States Patent
Enomura et al.

(10) Patent No.: US 11,617,720 B2
(45) Date of Patent: *Apr. 4, 2023

(54) MAIN AGENT UNIFORMLY DISPERSED MICROSPHERE AND A SUSTAINED RELEASE FORMULATION COMPRISING THE SAME

(71) Applicant: M. TECHNIQUE CO., LTD., Izumi (JP)

(72) Inventors: Masakazu Enomura, Izumi (JP); Kaeko Araki, Izumi (JP); Mai Yoshizumi, Izumi (JP)

(73) Assignee: M. TECHNIQUE CO., LTD., Izumi (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/269,002

(22) PCT Filed: Nov. 27, 2020

(86) PCT No.: PCT/JP2020/044366
§ 371 (c)(1),
(2) Date: Feb. 17, 2021

(87) PCT Pub. No.: WO2021/225013
PCT Pub. Date: Nov. 11, 2021

(65) Prior Publication Data
US 2021/0346298 A1 Nov. 11, 2021

(30) Foreign Application Priority Data

May 8, 2020 (WO) .................. PCT/JP2020/018731
Sep. 11, 2020 (WO) .................. PCT/JP2020/034524

(51) Int. Cl.
| | |
|---|---|
| *A61K 9/16* | (2006.01) |
| *A61K 31/12* | (2006.01) |
| *A61K 31/095* | (2006.01) |
| *A61K 31/57* | (2006.01) |
| *A61K 31/496* | (2006.01) |
| *A61K 31/7048* | (2006.01) |

(52) U.S. Cl.
CPC .......... *A61K 9/1647* (2013.01); *A61K 9/1652* (2013.01); *A61K 31/095* (2013.01); *A61K 31/12* (2013.01); *A61K 31/496* (2013.01); *A61K 31/57* (2013.01); *A61K 31/7048* (2013.01)

(58) Field of Classification Search
None
See application file for complete search history.

(56) References Cited

U.S. PATENT DOCUMENTS

| 5,945,126 A | 8/1999 | Thanoo et al. |
|---|---|---|
| 2006/0134223 A1 | 6/2006 | Yamada |
| 2007/0059363 A1 | 3/2007 | Lee et al. |
| 2008/0102131 A1 | 5/2008 | Nagira et al. |
| 2009/0004283 A1 | 1/2009 | Petersen et al. |
| 2010/0155310 A1 | 6/2010 | Enomura |
| 2010/0203151 A1 | 8/2010 | Hiraoka |
| 2010/0272820 A1 | 10/2010 | Lim et al. |
| 2014/0341997 A1 | 11/2014 | Kim et al. |
| 2015/0321154 A1 | 11/2015 | Enomura |
| 2016/0089335 A1 | 3/2016 | Ohri et al. |
| 2017/0281547 A1 | 10/2017 | Karavas et al. |

FOREIGN PATENT DOCUMENTS

| CN | 103054809 A * | 4/2013 |
|---|---|---|
| EP | 0 442 671 B1 | 6/1995 |
| JP | 4-114725 A | 4/1992 |
| JP | 2653255 B2 | 9/1997 |
| JP | 2001-512461 A | 8/2001 |
| JP | 2002-534392 A | 10/2002 |
| JP | 2005-15476 A | 1/2005 |
| JP | 2005-35994 A | 2/2005 |
| JP | 2009-520727 A | 5/2009 |
| JP | 2009-132871 A | 6/2009 |

(Continued)

OTHER PUBLICATIONS

International Search Report, issued in PCT/JP2020/044366, dated Jan. 12, 2021, with English translation.
Kikuchi, Drug Delivery System, 2014, vol. 29, No. 1, pp. 51-63.
Written Opinion of the International Searching Authority, issued in PCT/JP2020/044366, dated Jan. 12, 2021, with English Translation.
Chinese Office Action and Search Report for Chinese Application No. 202080025520.1, dated Aug. 12, 2022, with an English translation of the Chinese Office Action.

*Primary Examiner* — Bethany P Barham
*Assistant Examiner* — Peter Anthopolos
(74) *Attorney, Agent, or Firm* — Birch, Stewart, Kolasch & Birch, LLP

(57) ABSTRACT

The present application provides a microsphere in which a main agent is uniformly dispersed in a polymer matrix, wherein an average volume-based particle diameter of the microsphere is 1 μm or more and 150 μm or less, and a variation coefficient of area ratios in four regions is 0.35 or less, wherein the area ratios in four regions are calculated by (s/A)×100(%) wherein the four regions are prepared by preparing a cross section observation sample obtained by cutting the microsphere; observing the cross section observation sample with an electron microscope at a magnification capable of confirming the main agent in the microsphere or a higher magnification; and dividing the electron microscope observation image into four regions; and A is an area of a respective divided region, and s is a sum of cross section areas of the main agent included in the respective divided region. The microsphere of the present invention can appropriately control the initial release amount of the main agent and its release rate during a subsequent release period, and can continuously release the main agent for a predetermined period of time.

4 Claims, 9 Drawing Sheets

(56) References Cited

FOREIGN PATENT DOCUMENTS

| | | |
|---|---|---|
| JP | 2010-510206 A | 4/2010 |
| JP | 2010-531303 A | 9/2010 |
| JP | 2011-189348 A | 9/2011 |
| JP | 5147091 B1 | 2/2013 |
| JP | 2014-224114 A | 12/2014 |
| JP | 2016-69378 A | 5/2016 |
| JP | 2017-509661 A | 4/2017 |
| WO | WO 00/40259 A1 | 7/2000 |
| WO | WO 2008/053920 A1 | 5/2008 |

* cited by examiner

MAIN AGENT UNIFORMLY DISPERSED MICROSPHERE AND A SUSTAINED RELEASE FORMULATION COMPRISING THE SAME

TECHNICAL FIELD

The present inventions relate to a microsphere in which a main agent is uniformly dispersed and a sustained release formulation comprising the same. The present inventions specifically relate to a microsphere in which a main agent is uniformly dispersed in a biodegradable polymer matrix, and a sustained release formulation comprising the same.

BACKGROUND ART

Recently, a microsphere or nanosphere has attracted attention as a sustained release formulation of a medicine containing a main agent or the like. A microsphere generally refers to a formulation having a particle diameter of 1 μm to about 150 μm, and a formulation smaller than that having a particle diameter less than 1 μm is referred to as a nanosphere. For example, when a main agent is incorporated in a biodegradable synthetic or natural polymer, the main agent can be continuously released locally, or the main agent can be targeted to a tissue.

A sustained release microsphere formulation which gradually releases a main agent at a constant rate, needs to be, for example, a formulation in which a biodegradable polymer, a main agent, an additive, a solvent and the like are appropriately controlled. In order for a sustained release microsphere formulation to effectively exhibit a pharmacological effect in vivo for a predetermined period of time, it is necessary to continuously release the main agent in vivo for a predetermined period of time, by appropriately controlling the initial release amount of the main agent and its release rate during a subsequent release period. However, in the case of conventional microspheres, the initial burst occurs by 10 to 30% after administration, so it cannot be used with a medicine that require control of a concentration in blood or a tissue such as insulin and an anticancer agent. If this initial burst is resolved conversely, utility value of a long-term sustained release microsphere is expected to increase (Non-Patent Literature 1).

A particle diameter of the microsphere and a dispersion state of the main agent in the microsphere are related, in order to suppress an abnormal initial release amount (an initial burst) of the main agent and to control its release rate during a release period to be constant. In spite of a problem of yield, the particle diameter of the microsphere can be adjusted to a desired particle diameter by an operation such as filtration. However, the dispersion state of the biologically active substance in the microsphere has been reported only as uniform, and has not been confirmed.

Patent Literature 1 discloses a formulation as a long-term sustained release microcapsule which releases leuprorelin acetate of a luteinizing hormone releasing hormone derivative, during from about 1 month to several months by subcutaneous injection. The formulation has a problem that a distribution of the particle diameters is very wide from 1 μm to 400 μm. Therefore, Patent Literature 2 proposes as a method for solving this problem, a method of producing a microsphere in which a main agent is encapsulated in a polymer for a carrier by a double emulsification method. However, Patent Literature 2 does not describe the dispersion state of the medicine in the leuprorelin acetate containing microspheres obtained in Examples 1 to 5.

Patent Literature 3 discloses a microsphere which reduces a chronic pain for at least 28 days (672 hours). The microsphere comprises a biodegradable polymer and a local anesthetic (a main agent), and releases about 75% of the local anesthetic during about 72 hours, and about 80 to 90% of the local anesthetic during about 120 hours. This suggests that the distribution of the local anesthetic in the microsphere is not uniform in the microsphere, and is biased in the outer side. From the SEM (scanning electron microscope) image of a cross section of the microsphere described in FIG. 2, the dispersion state of the local anesthetic cannot be confirmed.

Patent Literature 4 discloses a core shell structure microsphere in which a core contains solid aripiprazole, and the surface of the core is coated with a shell containing a biodegradable polymer. As described above, the microsphere of Patent Literature 4 is not a microsphere in which the main agent is uniformly dispersed. Further, in the electron microscope photograph of a cross section obtained by cutting the microsphere obtained in the example shown in FIG. 5, the dispersion state of aripiprazole cannot be confirmed in the shell.

Patent Document 5 discloses that an oily component containing a lipophilic substance as a main agent is polydispersed in a polymer matrix composed of a water-soluble excipient containing a water-soluble polymer as a main component. In Patent Literature 5, a particle diameter is confirmed by dissolving the water-soluble polymer matrix and measuring a particle diameter distribution of the main agent, but an actual dispersion state of the main agent in the water-soluble polymer matrix is not confirmed.

CITATION LIST

Patent Literature

Patent Literature 1: JP 2653255
Patent Literature 2: JP 2014-224114
Patent Literature 3: JP 2016-069378
Patent Literature 4: JP 2010-531303
Patent Literature 5: WO 2008/053920

Non-Patent Literature

Non Patent Literature 1: Drug Delivery System, 2014, Vol. 29, No. 1, pp. 51-63

SUMMARY OF THE INVENTION

Technical Problem

A biodegradable polymer microsphere having an average volume-based particle diameter of 1 μm or more and 150 μm or less cannot be put in practice as its release period is designed, unless distribution of a main agent (hereinafter, may be referred to as a medicine) in the microsphere is controlled. For example, when the main agent is biased near the surface of the microsphere, a large amount of the main agent is released from the microsphere in the initial period after administration to generate the problem of the initial burst. On the other hand, when the main agent is biased in the center of the microsphere or when the microsphere is in a state of a core shell structure, the main agent cannot be released continuously from the initial period. Therefore, a state in which the main agent is uniformly dispersed in the microparticle, is desirable. When it is in a dispersed state in which large masses of the main agent are scattered, the main agent cannot be released continuously from the initial period. Similarly, when empty holes are not controlled, a similar problem occurs in the release of the main agent.

When pharmacokinetics are actually investigated using a small animal such as a rat, many variations in the release rate and release profile sometimes occur. The reason is often concluded as an individual difference of rats. However, if the dispersion state of a main agent in the microsphere is uniform, most of the variations will be more improved, and decomposition rate will be controlled by a kind and molecular weight of the polymer, and release of the main agent from the microsphere can be realized as designed.

Uniform dispersion of the main agent in the microsphere is the absolute condition for continuously releasing the main agent in vivo for a predetermined period of time. However, the uniform dispersion state of the main agent in the microsphere has not been searched at present. Since the particle diameter of the microsphere is large unlike that of the nanoparticle, homogenization of the microsphere is generally difficult. Therefore, it is necessary to confirm the dispersion state of the main agent in the microsphere. For that, a cross section observation sample obtained by cutting a microsphere particle is prepared, and is observed with an electron microscope at a magnification capable of confirming the main agent in the microsphere or a higher magnification, so that the dispersion state can be confirmed. This can be easily performed, and is certain.

FIG. 1 is an electron micrograph of the microcapsule sustained release formulation leuplin (registered trademark) for injection 1.88 mg (Takeda Pharmaceutical Company Limited), which corresponds to the sustained release microcapsule of a LH-RH derivative described in Patent Literature 1.

The formulation includes various sizes of particles from large particles to small particles. FIG. 2 is an SEM (scanning electron microscope) image of a cross section of the particle of about 6 μm which was selected as a representative particle. It is understood by confirmation of an edge effect in an image, or by an SEM-EDS (energy dispersive X-ray spectrometer), that large dispersion bodies indicated by arrows in FIG. 2 are empty holes. FIG. 3 is an image prepared by dividing the SEM cross section image of FIG. 2 into four regions (Region 1 to Region 4); an averaging process in the pixel range of 3×3 using a commercial image analysis software iTEM (TEM camera control, image analysis software, EMSIS GmbH); contrast optimization by a process of highlighting the edge part; a binarization process; a process of removing noises and highlighting particles with low contrast by image processing; a second averaging process in the pixel range of 3×3; and a process of highlighting the edge part. Based on FIG. 3, a variation coefficient of the area ratios: $(s/A) \times 100(\%)$, wherein A is an area of a respective divided region, and s is a sum of cross section areas of the main agent included in the respective divided region, was calculated, and the variation coefficient was 1.114. By performing in this way, the dispersion state of the main agent can be confirmed from the cross section. Since the variation coefficient exceeds 0.35, and the main agent is not uniformly dispersed in the microsphere particle, the formulation cannot appropriately control the release rate during the release period.

Accordingly, an object of the present invention is to provide a microsphere capable of appropriately controlling the initial release amount of a main agent and its release rate during a subsequent release period, and continuously releasing the main agent in vivo for a predetermined period of time.

Solution to the Problem

The present inventors earnestly studied to solve the above problem. As a result of that, the present inventors have found that by a microsphere wherein a variation coefficient of area ratios of a main agent in a respective region prepared by electron microscope observation of a cross section of the microsphere followed by dividing the cross section observation image into four regions, is 0.35 or less, the main agent is uniformly dispersed in the microsphere, empty holes are not present, and the microsphere can appropriately control the initial release amount of the main agent and its release rate during a subsequent release period, and can continuously release the main agent in vivo for a predetermined period of time. Thus, the present inventors have accomplished the present inventions. Namely, the present inventions are as follows.

[1] The first embodiment of the present invention is a microsphere in which a main agent is uniformly dispersed in a polymer matrix, wherein an average volume-based particle diameter of the microsphere is 1 μm or more and 150 μm or less, and a variation coefficient of area ratios in four regions is 0.35 or less, wherein the area ratios in four regions are calculated by $(s/A) \times 100(\%)$ wherein the four regions are prepared by preparing a cross section observation sample obtained by cutting the microsphere; observing the cross section observation sample with an electron microscope at a magnification capable of confirming the main agent in the microsphere or a higher magnification; and dividing the electron microscope observation image into four regions; and A is an area of a respective divided region, and s is a sum of cross section areas of the main agent included in the respective divided region.

[2] The second embodiment of the present invention is the microsphere according to [1], wherein the main agent is a lipophilic substance.

[3] The third embodiment of the present invention is the microsphere according to [1] or [2], wherein an average volume-based particle diameter of the dispersed main agent is 5 nm to 500 nm.

[4] The fourth embodiment of the present invention is the microsphere according to any one of [1] to [4], wherein a content of the main agent in the microsphere is 0.10 to 50% by mass relative to the total amount of the microsphere.

[5] The fifth embodiment of the present invention is the microsphere according to any one of [1] to [3], wherein the polymer is a biodegradable polymer.

[6] The sixth embodiment of the present invention is a sustained release formulation comprising the microsphere according to any one of [1] to [5].

Advantageous Effects of the Invention

The microsphere of the present invention can appropriately control the initial release amount of a main agent and its release rate during a subsequent release period, and can continuously release the main agent for a predetermined period of time.

BRIEF DESCRIPTION OF THE DRAWINGS

FIG. 6-1 shows an SEM image of a cross section of the microsphere of Example 1.

FIG. 6-2 shows an image prepared by dividing the cross section image of FIG. 6-1 into four regions and a binarization process, for calculating area ratios: (s/A)×100(%), wherein A is an area of a respective divided region, and s is a sum of cross section areas of the main agent included in the respective divided region.

FIG. 7-1 shows an SEM image of a cross section of the microsphere of Example 3.

FIG. 7-2 shows an image prepared by enlarging the cross section image of FIG. 7-1 and a binarization process.

FIG. 8-1 shows an SEM image of a cross section of the microsphere of Example 4.

FIG. 8-2 shows an image prepared by a binarization process of the cross section image of FIG. 8-1.

DESCRIPTION OF THE INVENTION

1. Microsphere

Figure 1:
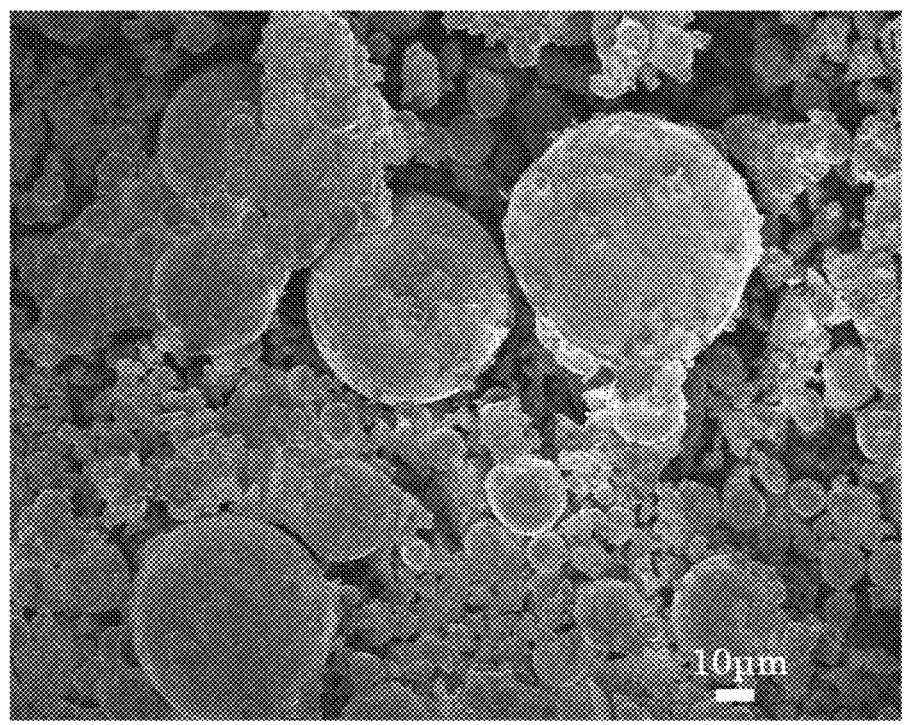
FIG. 1 shows an SEM (scanning electron microscope) image of leuplin (registered trademark) for injection 1.88 mg (Takeda Pharmaceutical Company Limited).

The microsphere of the present invention is a microsphere in which a main agent is uniformly dispersed in a polymer matrix, wherein an average volume-based particle diameter of the microsphere is 1 μm to 150 μm, and a variation coefficient of area ratios in four regions is 0.35 or less, wherein the area ratios in four regions are calculated by (s/A)×100(%) wherein the four regions are prepared by preparing a cross section observation sample obtained by cutting the microsphere; observing the cross section observation sample with an electron microscope at a magnification capable of confirming the main agent in the microsphere or a higher magnification; and dividing the electron microscope observation image into four regions; and A is an area of a respective divided region, and s is a sum of cross section areas of the main agent included in the respective divided region.

When a main agent is biased in the surface layer or in the center of the microsphere, or when coarse particles, aggregates or large empty holes, etc. are present in the microsphere, the above variation coefficient of area ratios becomes large. When the above variation coefficient of area ratios is 0.35 or less, the main agent is in a uniformly dispersed state. In the microsphere of the present invention, the variation coefficient of area ratios of occupation of the main agent relative to the area of the respective region, in the respective region obtained by dividing a cross section of the microsphere into four regions, is 0.35 or less, preferably 0.25 or less, more preferably 0.20 or less.

The microsphere of the present invention can appropriately control the initial release amount of the main agent and its release rate during a subsequent release period, and can continuously release the main agent in vivo for a predetermined period of time.

<Observation of Cross Section of Microsphere>

A method of confirming a dispersion state of a main agent in the microsphere is explained below.

The method can be performed by observing a cross section of the microsphere with an electron microscope at a magnification capable of clearly confirming the dispersed microparticles of the main agent. The electron microscope includes a transmission electron microscope (TEM) using transmitted electrons as an information source, a scanning electron microscope (SEM) detecting secondary electrons (backscattered electrons), etc. The electron microscope may be selected according to the sample to be observed. The fine structure of nanospheres can be more observed with a transmission electron microscope. Presence or absence of empty holes of 500 nm or more and/or segregation of the main agent, etc. in the microsphere, can be observed by using a phase contrast microscope or the like. When empty holes or inclusions are segregated, a refractive index is changed, and thus difference of contrast within a microsphere particle occurs. It is simple and useful when the difference is larger than the size of the wavelengths of light.

The observation method is not particularly limited, but specifically, it can be confirmed by the following method. At first, the microsphere is coated with a thin film of gold, platinum, platinum/palladium alloy, etc. In Examples, the microspheres are coated with osmium. Then, the microsphere is first frozen with liquid nitrogen. After frozen, a cross section of FIB (focused ion beam) is prepared. That is, a cross section observation sample of the microsphere is prepared by irradiating a focused ion beam onto a sample using an FIB apparatus, and cutting out a structure at a desired position inside the sample. A preferable particle diameter of the microparticles of the main agent dispersed in the polymer matrix is several tens nm to several hundreds nm, but the particle diameter may be several μm in some cases. An entire cross section of the microsphere is observed at an observation magnification of an electron microscope capable of confirming the dispersed microparticles of the above preferable particle diameter. Usually, an observation magnification of an electron microscope is from 2,500 to several hundreds of thousands. In addition, in the case where a higher magnification at which the entire microsphere cannot be observed is used, the observed portions may be joined to observe the entire microsphere.

Figure 5:
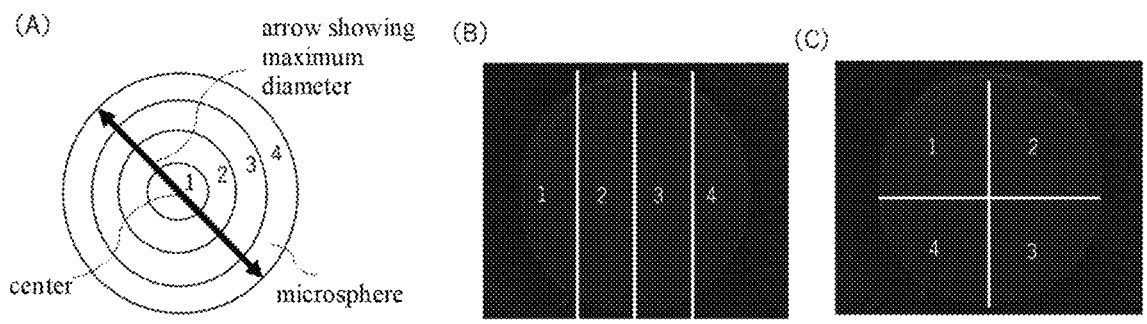
FIG. 5 shows examples of a method of dividing a microsphere. (A) shows an example of dividing it into four regions concentrically. (B) shows an example of dividing it into four regions longitudinally. (C) shows an example of dividing it into four regions latitudinally.

When the cross section image is divided into four regions, for example, as shown in FIGS. 5A to 5C, the cross section image may be divided into four regions concentrically, or may be divided into four regions in the vertical or horizontal direction, or may be divided into four regions latitudinally from the center. It is preferable to take a dividing method that remarkably shows a segregation state of the main agent. For example, when dividing into four regions concentrically (FIG. 5A), it is essential to divide concentrically by dividing the radius into four equal parts from the center point of the maximum diameter of the cross section of the microsphere. When dividing into four regions in the vertical or horizontal direction (FIG. 5B), it is essential to divide into four regions at equal intervals. It is essential to divide into four regions in either direction parallel or perpendicular to the above maximum diameter. When dividing into four regions latitudinally from the center (FIG. 5C), it is essential to divide into four regions latitudinally every 90° around the center point of the above maximum diameter as a center. Depending on the constituent elements of the main agent, an elementary analysis may be performed by analyzing the cross section of the microsphere using an EDS (Energy Dispersive X-ray Spectrometer), and it can be also confirmed whether or not it is an empty hole. In the case of empty holes, it should not be integrated into the area of the main agent. When the EDS detection elements are not contained, the cross section observation sample may be stained with ruthenium tetroxide, osmium tetroxide, phosphotungstic acid, uranyl acetate, samarium acetate, iodine or the like. It is also possible to identify the main agent by comparison with a microsphere without the main agent. The staining method is effective when it is difficult to obtain contrast in the electron microscope cross section observation image. The above are explained just as examples, and the sample may be embedded with a resin, or a microtome may be used to prepare a cross section of the microsphere.

A method of calculating a cross section area is not particularly limited, but it is preferable to use a commercial image analysis software. As a commercial image analysis software, various kind of software such as Image-Pro Plus (Media Cybernetics, Inc.), iTEM (TEM camera control, image analysis software, EMSIS GmbH), etc. can be used.

<Polymer>

As a polymer used in the microsphere of the present invention, a polymer can be utilized, which includes a polyester or a copolymer thereof such as polylactide (polylactic acid, PLA), poly (D-lactide), poly (L-lactide), poly (DL-lactide), polyglycolide (polyglycolic acid, PGA), poly (lactide-co-glycolide) (polylactic-co-glycolic acid, PLGA), poly (D-lactide-co-glycolide), poly (L-lactide-co-glycolide), poly (DL-lactide-co-glycolide), polycaprolactone (PCL), polycarbonate, polyesteramide, polyanhydride, polyorthoester, polyether ester, poly (dioxanone), copolymers of polyethylene glycol and polyorthoester, polybutylene succinate, etc.; a cellulose or a cellulose derivative such as cellulose acetate (CA), ethyl cellulose (EC), hydroxypropyl cellulose, hydroxypropyl methyl cellulose, carboxymethyl cellulose, etc.; a polysaccharide or a derivative thereof such as amylose, amylopectin, pectin, starch, chitosan, mannan, cyclodextrin, galaginan, etc.; a polyacetal, polyamino acid, polycyanoacrylate, polyalkylene alkylate, biodegradable polyurethane mixture or a copolymer thereof, polyvinyl acetate, methacrylic acid copolymer, collagen, gelatin, etc. The polymers described in the present specification are described as examples, and a polymer is not limited to the described polymers. In addition, a polymer can be appropriately selected depending on a kind of a medicine, release rate, etc., and may be used alone or in combination of a plurality of polymers.

A non-biodegradable polymer may be used when it is necessary to maintain a sustained release effect of a main agent in vivo for a long time. A biodegradable polymer may be used when it is necessary to release a medicine in a short time. In addition, for example, biodegradation rates of poly (caprolactone), poly (lactide) and poly (lactide-co-glycolide) are higher in this order, and therefore, a sustained release rate of the medicine can also be controlled by selection of a polymer forming the microsphere.

Regarding constitution of a polymer, a molar ratio, etc is not particularly limited, and may be appropriately selected according to the intended purpose. For example, the molar ratio (L:G) of the constitutional unit (L) derived from lactic acid and the constitutional unit (G) derived from glycolic acid in PLGA is not particularly limited, and may be appropriately selected according to the intended purpose. A preferable molar ratio (L:G) is 1:99 to 99:1, more preferably 25:75 to 99:1, further preferably 30:70 to 90:10, particularly preferably 50:50 to 85:15. Only PLA or PGA may be used. A molar ratio of constitutional units in other co-polymers may be adjusted similarly. Selection of its molecular weight is also important for realizing a uniform dispersion state of a main agent.

The microsphere of the present invention includes a main agent in a polymer matrix. The microsphere may further contain a dispersing agent and another component, if necessary. A state of the polymer matrix is not particularly limited, and may be appropriately in an amorphous state.

[Main Agent]

A main agent contained in the microsphere of the present invention is not particularly limited, and may be appropriately selected according to the intended purpose. The main agent may be, for example, a pharmaceutical compound, a functional food compound, a functional cosmetic compound, an animal administration compound, an agricultural compound and the like. A microsphere containing a pharmaceutical compound can be suitably used, for example, as a sustained release pharmaceutical formulation. The main agent includes both a lipophilic substance and a hydrophilic substance. A preferable main agent includes a lipophilic substance. The lipophilic substance means, for example, a substance having a log P value of water/octanol distribution coefficient of 3 or more, and a main agent not contained in a lipophilic substance is classified as the hydrophilic substance. The water/octanol distribution coefficient can be measured according to the Japanese Industrial Standard: JIS Z 7260-107 (2000): Flask shaking method. The main agent is not particularly limited as long as a sustained release formulation comprising the main agent is desired, and may be appropriately selected according to the intended purpose. The main agent includes any form of a salt, hydrate, and the like.

The main agent is uniformly dispersed in the microsphere of the present invention. By adopting such constitution, the microsphere can appropriately control the initial release amount of the main agent and its release rate during a subsequent release period, and can continuously release the main agent for a predetermined period of time. Uniform dispersion of the main agent in the microsphere can be controlled by the content of the main agent, relative to the total amount of the microsphere. A preferable content of the main agent varies depending on the main agent, and is, for example, 0.1 to 50% by mass, preferably 0.3 to 30% by mass, more preferably 0.35 to 15% by mass, further more preferably 0.5 to 10% by mass, relative to the total amount of the microsphere.

The average volume-based particle diameter of the dispersed microparticles of the main agent is preferably 5 nm to 500 nm, more preferably 10 nm to 400 nm, and further preferably 20 nm to 200 nm.

[Dispersing Agent]

A dispersing agent may be used for dispersing the main agent. The dispersing agent may be a low molecular weight dispersing agent or a high molecular weight polymer dispersing agent. A low molecular weight dispersing agent means a compound having a mass average molecular weight less than 15,000. A high molecular weight polymer dispersing agent means a compound having a mass average molecular weight of 15,000 or more, including repeated covalent bonds between one or more of monomers.

The low molecular weight dispersing agent is not particularly limited as long as it is acceptable for a pharmaceutical compound, a functional food compound, a functional cosmetic compound, an animal administration compound, an agricultural compound and the like, and may be appropriately selected according to the intended purpose. A specific example thereof includes a lipid, a saccharide, an amino acid, an organic acid, another component, and the like. These may be used alone or in combination of two kinds or more thereof.

The lipid is not particularly limited, and may be appropriately selected according to the intended purpose. The lipid may be, for example, a medium chain or long chain monoglyceride, diglyceride or triglyceride, a phospholipid, a vegetable oil (e.g. soybean oil, avocado oil, squalene oil, sesame oil, olive oil, corn oil, rape-seed oil, safflower oil, sunflower oil, etc.), a fish oil, a flavoring oil, a water-insoluble vitamin, a fatty acid, and a mixture thereof, a derivative thereof and the like. These may be used alone or in combination of two kinds or more thereof.

The sugar is not particularly limited, and may be appropriately selected according to the intended purpose. The sugar includes, for example, glucose, mannose, idose, galactose, fucose, ribose, xylose, lactose, sucrose, maltose, trehalose, turanose, raffinose, maltotriose, acarbose, water-soluble cellulose, synthetic cellulose, sugar alcohol, glycerin, sorbitol, lactitol, maltitol, mannitol, xylitol, erythritol, polyol, and a derivative thereof, and the like. These may be used alone or in combination of two kinds or more thereof.

The another component is not particularly limited and may be appropriately selected according to the intended purpose. The another component is preferably one which can be used for a medicine, a food, cosmetics, etc.

<Average Volume-Based Particle Diameter>

The average volume-based particle diameter of the microsphere of the present invention is 1 μm or more and 150 μm or less, preferably 10 μm or more and 100 μm or less, and more preferably 20 μm or more and 75 μm or less. The average volume-based particle diameter may be measured using a laser diffraction particle size distribution measuring apparatus. In the present invention, when the average volume-based particle diameter exceeds 150 μm, the problem of an initial burst occurs due to non-uniform dispersibility of the main agent in the microsphere particles, which tends to cause aggregation and sedimentation, and to lead to difficult processing in a subsequent step. When the average volume-based particle diameter is smaller than 1 μm, the problem of an initial burst occurs remarkably.

The microsphere of the present invention can appropriately control the initial release amount of a main agent and its release rate during a subsequent release period, and can continuously release the main agent in vivo for a predetermined period of time.

2. Sustained Release Formulation

By using the microsphere of the present invention, a sustained release formulation containing the microsphere can be prepared. The sustained release formulation of the present invention can appropriately control the initial release amount of a main agent and its release rate during a subsequent release period, and can continuously release the main agent for a predetermined period of time, and a pharmacological effect can be effectively exhibited.

The sustained release formulation of the present invention can be simply administered as an injection, an implant or a transdermal formulation, directly to a lesion such as a muscle, subcutaneous tissue, blood vessel, organ, joint cavity, tumor, or the like. It may be administered by various other formulations such as an oral formulation, embrocation formulation, nasal drop formulation, etc. For example, when preparing a sustained-release preparation of the present invention as an injection formulation, the sustained release injection formulation as an aqueous suspension may be prepared together with a dispersing agent (Tween 80, HCO 60, carboxy methylcellulose, sodium alginate, etc.), a preservative (methylparaben, propylparaben, etc.), an isotonizing agent (sodium chloride, mannitol, sorbitol, glucose, etc.) and the like. Alternatively, the sustained release injection formulation as an oil suspension may be prepared with a vegetable oil such as soybean oil, sesame oil, corn oil, and the like. The sustained release formulation of the present invention can be administered in any one of the above forms.

3. Method of Producing Microsphere

<Step of Producing Microsphere>

The method of producing the microsphere of the present invention includes at least the step of forming particles, and may further include the step of filtration and sterilization, the step of removing a good solvent, and other steps, if necessary.

A method of drying emulsion in liquid using a solvent is explained in detail herein. However, a solvent free production method, a direct spray method of mixed liquid, etc. may be used.

<Step of Forming Particles>

The step of forming particles is not particularly limited, but it is preferable to use a pulverizing apparatus in which pulverization is performed between a plurality of processing surfaces being capable of approaching to and separating from each other, at least one of which rotates relative to the other, which is described in JP 2009-132871 or JP 2011-189348. The step of forming particles is performed, for example, by continuously feeding to the pulverizing apparatus a solution of a polymer containing a main agent obtained by dissolving or dispersing the polymer and the main agent in a good solvent of the polymer, and a solution containing a poor solvent of the polymer to prepare emulsified particles; and removing the good solvent from the produced particles to precipitate the microsphere of the present invention. Here, "dispersing" includes dispersing the main agent as a solid in a good solvent of the polymer; emulsifying the main agent in a good solvent of the polymer; forming a w/o emulsion containing an aqueous solution of a hydrophilic main agent and a good solvent of the polymer; and the like.

The step of forming particles is fundamentally performed by a step including emulsifying the polymer solution containing the main agent, and removing the solvent, etc., but is not particularly limited by it. The step of forming particles and the step of removing a good solvent can be simultaneously performed by using spray dry, etc.

The solution of a polymer and a main agent is not particularly limited as long as it is a solution in which the polymer and the main agent are dissolved or dispersed in a good solvent of the polymer, and may be appropriately selected according to the intended purpose. The good solvent is not particularly limited, and may be appropriately selected according to the intended purpose. The good solvent includes, for example, a halogenated aliphatic hydrocarbon (e.g., dichloromethane, dichloroethane, chloroform, etc.), an alcohol (e.g., methanol, ethanol, propanol, etc.), a ketone (e.g., acetone, methyl ethyl ketone, etc.), an ether (e.g., diethyl ether, dibutyl ether, 1,4-dioxane, etc.), an aliphatic hydrocarbon (e.g., n-hexane, cyclohexane, n-heptane, etc.), an aromatic hydrocarbon (e.g., benzene, toluene, xylene, etc.), an organic acid (e.g., acetic acid, propionic acid, etc.), an ester (e.g., methyl acetate, ethyl acetate, etc.), an amide (e.g., dimethyl amide, dimethyl acetamide, etc.), and the like. Water may be used in case of using a water soluble polymer. From the view point of the solubility, the good solvent is preferably a halogenated aliphatic hydrocarbon, an alcohol, a ketone, or a mixture thereof, more preferably dichloromethane, methanol, ethanol, acetone, methyl acetate, ethyl acetate or a mixture thereof. These may be used alone or in combination of two kinds or more thereof. The particle diameter and the amount of a medicine can be controlled by changing a kind of the solvent or a mixing amount of the solvent.

A good solvent means a solvent having high solubility of the polymer, and a poor solvent means a solvent having low or no solubility of the polymer. A good solvent and a poor solvent are selected so that the main agent is not biased in each microsphere, and a coarse particle or an aggregate of particles is not generated. In addition, a good solvent and a poor solvent can be defined by, for example, a quantity of the polymer which can be dissolved in 100 g of the solvent at 25° C. In the present invention, the good solvent is preferably a solvent which dissolves 0.1 g or more, more preferably 0.2 g or more, and still more preferably 0.5 g or more of the polymer. The poor solvent is preferably a solvent which dissolves only 0.05 g or less, more preferably 0.02 g or less, and still more preferably 0.01 g or less of the polymer. The poor solvent is not particularly limited, and may be appropriately selected according to the intended purpose, and water is preferable.

A content of the polymer in a solution of the polymer and a main agent may be changed depending on the good solvent, depending on the particle diameter of the intended microsphere, so that the main agent is uniformly dispersed in the microsphere. The content of the polymer is, for example, 1 to 30% by mass, preferably 3 to 20% by mass, and more preferably 5 to 15% by mass. The content of the main agent in the solution of the polymer may be appropriately changed according to the intended purpose, the pharmacological effect and the like, so that the main agent is uniformly dispersed in the microsphere.

A stabilizer may be added to the poor solvent for further ensuring stability of the produced microsphere. The stabilizer is not particularly limited, and may be appropriately selected according to the intended purpose. The stabilizer includes, for example, polyvinyl alcohol (PVA), polyvinyl pyrrolidone (PVP), carboxy methylcellulose (CMC), hydroxypropylcellulose (HPC), hydroxypropylmethylcellulose (HPMC), lecithin, Polysorbate 80, and the like, and polyvinyl alcohol (PVA) is preferable. Further, the concentration of the added stabilizer is preferably 0.01 to 20% by mass, more preferably 5% by mass or less. The preferable poor solvent is, for example, an aqueous solution of PVA, and the like.

The solution of a polymer and a main agent and the solution of a poor solvent is desirably prepared using a preparation apparatus such as a rotatory dispersing apparatus which realizes uniform mixing by applying a shearing force to a fluid, for example, by rotating a stirring bar of various shapes such as a rod, a plate and a propeller in a tank, or by equipping with a screen rotating relative to a stirring bar. A stirring apparatus disclosed in JP 5147091 may be applied as a preferable example of the rotatory dispersing apparatus. It is necessary to thoroughly mix the solution of the polymer and the poor solvent, for uniformly dispersing the main agent in the microsphere. For complete mixing, it is necessary to aim at homogenization at least on a molecular level. Incomplete mixing causes un-uniform dispersion state.

The rotatory dispersing apparatus may be a batch type one or a continuous type one. When performed by a continuous type rotatory dispersing apparatus, a stirring energy can be appropriately controlled, by using an apparatus to continuously supply and discharge a fluid to and from the stirring tank, or using a continuous mixer without using a stirring tank, or using a known stirring apparatus or a stirring means. Incidentally, the stirring energy is described in detail in JP H04-114725 by the present applicant. The stirring method in the present invention is not particularly limited, but may be performed using a various shearing type, friction type, high-pressure jet type, ultrasonic type, etc, of a stirrer, a dissolver, an emulsifier, a disperser, a homogenizer, or the like. An example thereof includes a continuous type emulsifier such as ULTRA-TURRAX (IKA-Werke GmbH & Co. KG), POLYTRON (Kinematica AG), TK HOMOMIXER (Primix Corporation), Ebara Milder (Ebara Corporation), TK HOMOMETIC LINE FLOW (Primix Corporation), Colloid Mill (Kobelko Eco-Solutions, Co., Ltd.), Slasher (NIPPON COKE & ENGINEERING, Co., Ltd.), Trigonal Wet Pulverizer (Mitsui Miike Chemical Engineering Machinery, Co., Ltd.), Cavitron (Euro Tech, Co., Ltd.), Fine Flow Mill (Pacific Machinery & Engineering, Co., Ltd.), and the like; a batch type or continuous dual type emulsifier such as Clearmix (M. Technique Co., Ltd.), Clearmix Dissolver (M. Technique Co., Ltd.), and the like. Further, it is desirable to use a stirring apparatus equipped with a stirring blade rotating at high speed and equipped with a screen outside of the stirring blade which discharges a fluid as a jet stream from an opening of the screen, particularly, the above Clearmix (M. Technique Co., Ltd.) and Clearmix Dissolver (M. Technique Co., Ltd.).

In the above pulverizing apparatus, it is possible to control the particle diameter and the particle diameter distribution of microparticles of the polymer matrix by adjusting the contact pressure of the rotating processing surfaces at a standstill period. As a result of experiments by the present inventors, the contact pressure is preferably 20 g/cm$^2$ to 250 g/cm$^2$. When the contact pressure is lower than 20 g/cm$^2$, the thin film is not stable and the particle diameter distribution becomes wide. When the contact pressure is higher than 250 g/cm$^2$, it has been found difficult to adjust the intended particle diameter. The contact pressure may be preferably 50 g/cm$^2$ to 200 g/cm$^2$, and more preferably 80 g/cm$^2$ to 150 g/cm$^2$.

It is preferable to prevent coalescence of the respective microspheres formed by contacting the solution of the polymer and the main agent with the solution containing the poor solvent. As a method of preventing the coalescence, the solution containing a poor solvent is preferably added in a tank for recovering a solution discharged fluid beforehand, and is slowly stirred. By stirring, the coalescence of the microspheres can be further suppressed. A rotatory dispersing apparatus is preferable for stirring, and Clearmix Dissolver (M. Technique Co., Ltd.) is desirable. The rotatory dispersing apparatus is not particularly limited as long as the whole solution can be made to flow mildly. When stirring is strong, the emulsified particles of the polymer may break down, the distribution width may become wider, and the dispersion state of the main agent in the polymer matrix may collapse.

When a main agent is a lipophilic substance, the step of forming particles can be suitably performed according to the above description, and a microsphere can be manufactured. When a main agent is a hydrophilic substance, the hydrophilic substance is dispersed in a good solvent of the polymer using, for example, a dispersing agent, whereby the step of forming particles can be similarly performed to produce a microsphere.

In addition, when a main agent is a hydrophilic substance, the hydrophilic substance is dissolved in an aqueous solvent such as water together with a stabilizer, if necessary, and is mixed with a polymer solution in which the polymer is dissolved in a good solvent of the polymer, to prepare a w/o emulsion; and the above step of forming particles is performed using the w/o emulsion as a solution of the polymer and the main agent, and using the above pulverizing apparatus. For preparing the w/o emulsion, an intermittent shaking method, a propeller type stirring apparatus, a method by a mixer using a turbine type stirring apparatus, a colloid mill method, a homogenizer method, and an ultrasonic irradiation method can be used. Using the above pulverizing apparatus, this w/o emulsion of the polymer solution containing the main agent, and a solution containing a poor solvent of the polymer are continuously added to prepare emulsified particles as a w/o/w emulsion; and the good solvent is removed from the produced particles to precipitate the microsphere of the present invention. This obtained microsphere may be used as it is, but it is also possible to further add an excipient (mannitol, sorbitol, lactose, glucose, etc.), redisperse the mixture, and freeze dry or spray dry the mixture, to be solidified. A more stable sustained release injection formulation can be obtained, by adding distilled water for injection or an appropriate dispersion medium to this solidified microsphere when used.

<Step of Filtration and Sterilization>

Sterile filtration of the prepared solution containing the polymer and the main agent and the solution of a poor solvent is preferably performed prior to the step pf forming particles, if desired. A bore diameter of the filter used for filtration is preferably 0.1 μm to 0.45 μm, more preferably 0.2 μm.

The above filter for sterile filtration is not particularly limited, and may be appropriately selected according to the intended purpose. For example, a hydrophilic filter such as polyvinylidene fluoride (PVDF) and polyethersulfone, and a hydrophobic filter such as polytetrafluoroethylene (PTFE), and the like may be used. The filter for sterile filtration is not limited to the material described here, but it is necessary to be selected depending on a kind of solvent used, and adsorption of the polymer, main agent or additive.

<Step of Removing a Good Solvent>

In the step of removing a good solvent, a good solvent is removed from the emulsified particles containing the polymer and the main agent. The step of removing a good solvent is not particularly limited, and may be appropriately selected according to the intended purpose, as long as the good solvent can be removed from the emulsified particles in the state that the main agent is uniformly dispersed in the microsphere. The step of removing a good solvent includes, for example, a method of evaporating and removing the good solvent from the fluid, by at least one of heating the fluid with stirring, flowing a gas such as nitrogen on a surface of the fluid, and reducing a pressure of the fluid. Flowing a gas such as nitrogen on a surface of the fluid is preferable. It is preferable in many cases to remove a good solvent quickly for maintaining the state that the main agent is uniformly dispersed in the microsphere. It is preferable in some cases to remove a good solvent slowly. A time of removing the good solvent may be, for example, 30 minutes to 12 hours, preferably 1 to 10 hours, and more preferably 1 to 5 hours.

A temperature in removing a good solvent depends on a kind of the good solvent. It is necessary to perform at a suitable temperature between a high temperature near the boiling point of the good solvent and a low temperature, while observing a cross section of the microsphere. The mixture may be diluted with a poor solvent for the purpose of removing the good solvent in the microsphere. Dilution with the poor solvent enables solidification of the surface of the microsphere as well as suppression of change of the particle diameter.

<Other Steps>

Other steps include, for example, a solvent composition preparation, a classification step, a particle cleaning step, and the like. Normally, coarse powder cut or fine powder cut is performed in the classification step, but the particles produced in the present invention do not substantially need the classification step. However, a classification step may be included just in case.

By the above production method, it is possible to produce a microsphere having a particle diameter of 1 μm to 150 μm in which a main agent is uniformly dispersed. Namely, it is possible to produce a microsphere wherein a variation coefficient of area ratios in four regions is 0.35 or less, wherein the area ratios in four regions are calculated by (s/A)×100(%) wherein the four regions are prepared by preparing a cross section observation sample obtained by cutting the microsphere; observing the cross section observation sample with an electron microscope at a magnification capable of confirming the main agent in the microsphere or a higher magnification; and dividing the observed image into four regions; and A is an area of a respective divided region, and s is a sum of cross section areas of the main agent included in the respective divided region.

EXAMPLE

Hereinafter, the present invention is explained in more detail with reference to Examples, but the present invention is not limited only to these Examples.

Reference Example 1

In Reference Example 1, microspheres (PLGA microparticles) without a main agent were prepared. Using the microspheres of Reference Example 1 as an index, cross sections of the microspheres of Examples and Comparative Examples were observed as SEM images, and the dispersion states of the main agent in the microspheres of Examples and Comparative Examples were confirmed below.

<Preparation of PLGA Solution and Aqueous PVA Solution>

Dichloromethane (Kanto Chemical Co., Inc.) was added to lactic acid-glycolic acid copolymer (Resomer RG504, Evonik AG) so that the concentration was 13% by mass. Lactic acid-glycolic acid copolymer was dissolved using a high-speed rotatory dispersing apparatus Clearmix Dissolver (M. Technique Co., Ltd.) to obtain PLGA solution. Thereafter, the solution was filtrated with a 0.2 μm vent filter (φ 62 mm, Merck KGaA). Ion exchanged water was added to polyvinyl alcohol (PVA, EG-40P, Nippon Synthetic Chemical Industry Co., Ltd.) so that the concentration was 1.5% by mass, and polyvinyl alcohol was dissolved using a high-speed rotatory dispersing apparatus Clearmix (M. Technique Co., Ltd.) to obtain an aqueous PVA solution. Thereafter, the solution was filtrated with a hydrophilic PVDF membrane filter (φ 47 mm, Merck KGaA). The aqueous PVA solution was added in a tank for collecting PLGA emulsified particles beforehand, and was slowly stirred to an extent that the solution surface just moved.

<Preparation of Microsphere (PLGA Microparticles)>

As the step of forming particles, the prepared PLGA solution and the aqueous PVA solution were mixed using the pulverizing apparatus described in JP 2011-189348. Here, the pulverizing apparatus described in JP 2011-189348 is an apparatus described in FIG. 25 of the publication, in which the opening of the second part d20 has a concentric annular shape which is surrounding the central opening of the processing surface 2 which is a ring-shaped disc, and a disk diameter is 75 mm. Specifically, the prepared aqueous PVA solution was introduced from the first introduction path d1 into the space between the processing surfaces 1 and 2 at 0.02 MPaG, at 65 mL/min and at 30° C., and the prepared PLGA solution was introduced from the second introduction path d2 into the space between the processing surfaces 1 and 2 at 0.65 MPaG, at 20 mL/min and at 30° C. at the rotational speed of the processing member 10 of 2,000 rpm, and the aqueous PVA solution and the PLGA solution were mixed in a forced thin film to prepare PLGA emulsified particles containing dichloromethane into the space between the processing surfaces 1 and 2. The fluid containing PLGA emulsified particles (hereinafter, PLGA emulsified particle dispersion) in the space between the processing surfaces 1 and 2 was discharged from the space between the processing surfaces 1 and 2 of the pulverizing apparatus. The discharged PLGA emulsified particle dispersion was collected in a recovery tank.

Next, as the step of removing a solvent, argon gas was blown onto the fluid surface to remove dichloromethane over 3.5 hours, while stirring the discharged fluid at a peripheral speed of 4.7 m/sec using Clearmix Dissolver (M. Technique Co., Ltd.), to obtain a suspension containing PLGA microparticles (PLGA microparticle suspension). The average volume-based particle diameter of the obtained PLGA microparticles was 34.0 μm. Representative particles were frozen with liquid nitrogen, and an FIB cross section was prepared, and an SEM image (FIG. 4) was observed.

Figure 4:
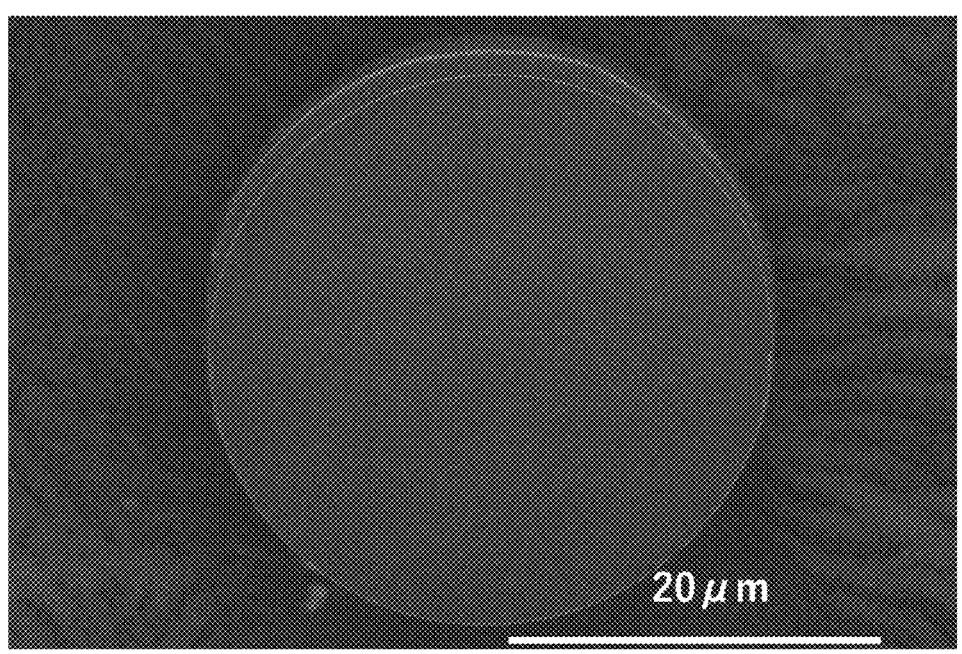
FIG. 4 shows an SEM image of a cross section of the microsphere without a main agent of Reference Example 1.

As shown in FIG. 4, it was confirmed that a particle-like mass or an empty hole was not present in the FIB section. Further, it was found that the cross section of the microsphere of Reference Example 1 could be used as an index in observation of cross sections of the microspheres of Examples and Comparative Examples.

Example 1

<Preparation of Solution of PLGA and Main Agent and Aqueous PVA Solution>

64.5% by mass of dichloromethane (Kanto Chemical Co., Inc.) and 25% by mass of acetone (Kanto Chemical Co., Inc.) were added to lactic acid-glycolic acid copolymer (Resomer RG752H, Evonik AG) and curcumin (FUJIFILM Wako Pure Chemical Corporation, Wako special grade) as a main agent, so that the concentration of lactic acid-glycolic acid copolymer was 10% by mass, and the concentration of curcumin was 0.5% by mass. Lactic acid-glycolic acid copolymer and curcumin were dissolved using a high-speed rotatory dispersing apparatus Clearmix Dissolver (M. Technique Co., Ltd.) to obtain a solution of PLGA and the main agent. Thereafter, the solution was filtrated with a 0.2 μm air vent filter (φ 62 mm, Merck KGaA). An aqueous PVA solution was prepared in the same manner as in Reference Example 1. The aqueous PVA solution was added in a tank for collecting emulsified particles of PLGA and the main agent beforehand, and was slowly stirred to an extent that the solution surface just moved.

<Preparation of Microsphere>

As the step of forming particles, the prepared solution of PLGA and the main agent and the aqueous PVA solution were mixed using the pulverizing apparatus described in JP 2011-189348 in the same manner as in Reference Example 1. Specifically, the prepared aqueous PVA solution was introduced from the first introduction path d1 into the space between the processing surfaces 1 and 2 at 0.01 MPaG, at 50 mL/min and at 25° C., and the prepared solution of PLGA and the main agent was introduced from the second introduction path d2 into the space between the processing surfaces 1 and 2 at 0.3 MPaG, at 16 mL/min of 25° C. at the rotational speed of the processing member 10 of 5,000 rpm, and the aqueous PVA solution and the solution of PLGA and the main agent were mixed in a forced thin film to prepare emulsified particles of PLGA and the main agent containing dichloromethane in the space between the processing surfaces 1 and 2. The fluid containing the emulsified particles of PLGA and the main agent (hereinafter, emulsified particle dispersion of PLGA and the main agent) in the space between the processing surfaces 1 and 2 was discharged from the space between the processing surfaces 1 and 2 of the pulverizing apparatus. The emulsified particle dispersion of PLGA and the main agent was collected in a recovery tank keeping the pressure of 0.03 MPaG.

Figure 2:
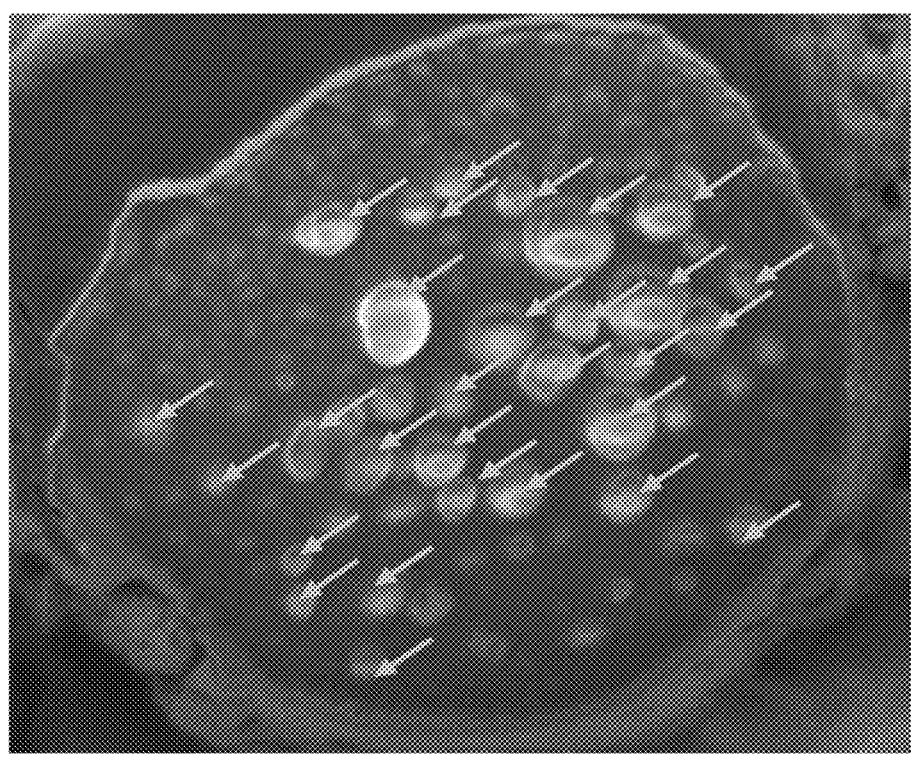
FIG. 2 shows an SEM image of a cross section of a representative particle of leuplin (registered trademark) for injection 1.88 mg (Takeda Pharmaceutical Company Limited).
Figure 3:
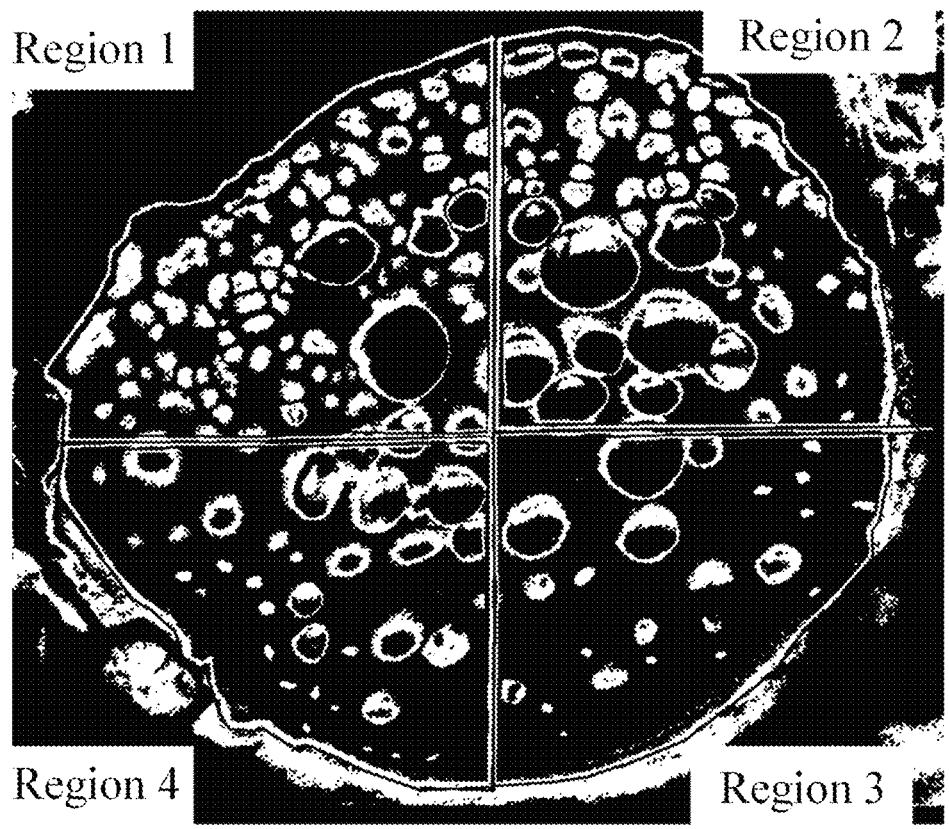
FIG. 3 shows an image prepared by dividing the cross section image of FIG. 2 into four regions and a binarization process, for calculating area ratios: (s/A)×100(%), wherein A is an area of a respective divided region, and s is a sum of cross section areas of the main agent included in the respective divided region.
Figures 1, 6:
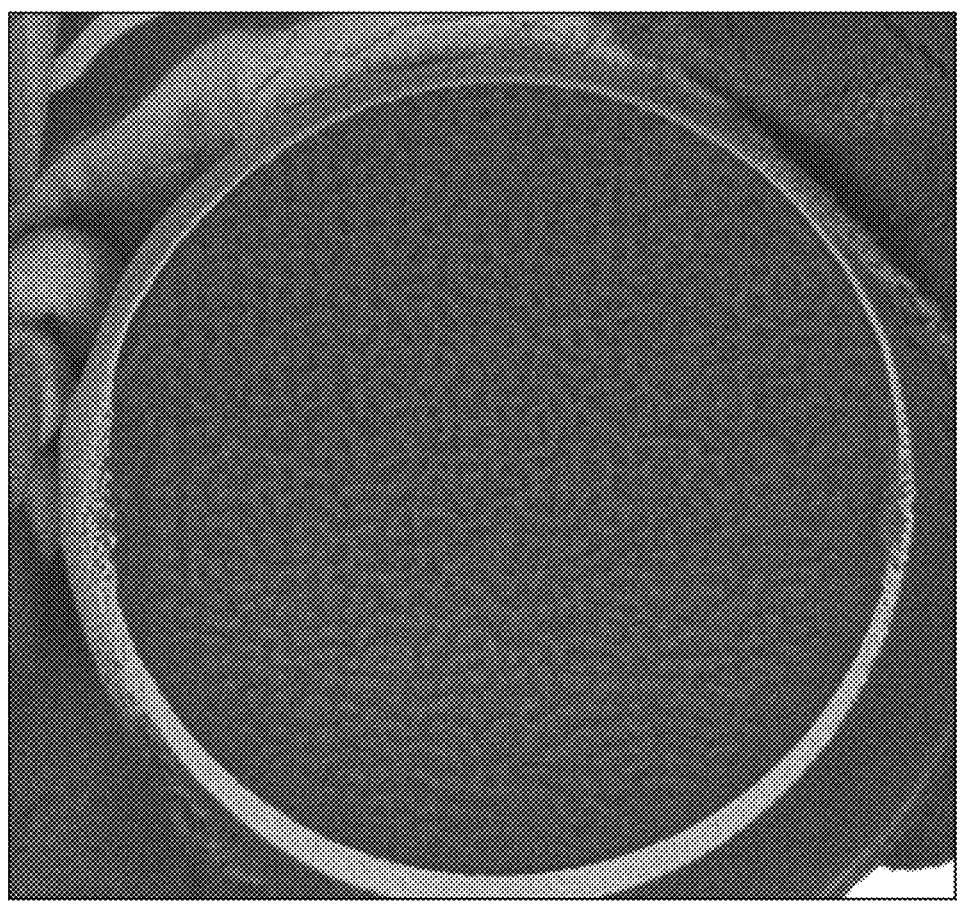
Figures 2, 6:
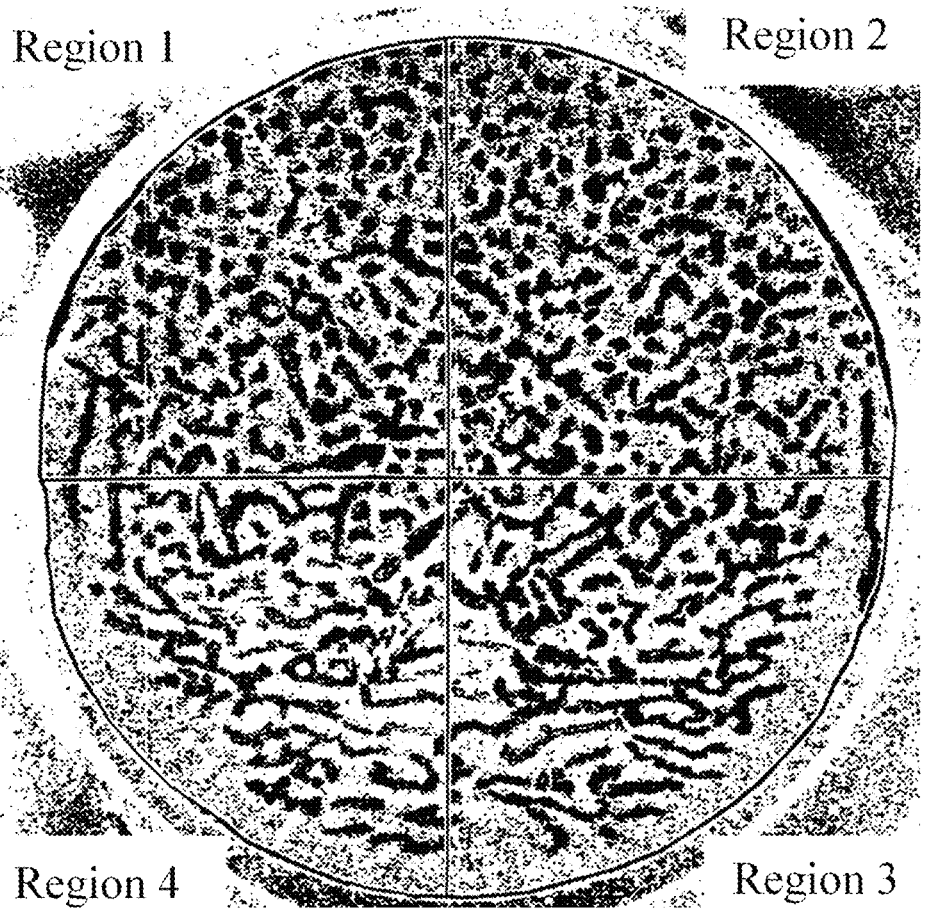

Next, as the step of removing a solvent, argon gas was blown on the fluid surface to remove dichloromethane and acetone over 3.5 hours, while stirring the discharged fluid at a peripheral speed of 4.7 m/sec using Clearmix Dissolver (M. Technique Co., Ltd.), to obtain a suspension containing microspheres (microsphere suspension). The average volume-based particle diameter of the obtained microspheres was 7.5 μm. Representative particles were frozen with liquid nitrogen, and an FIB cross section was prepared, and an SEM image (FIG. 6-1) was observed. To the obtained particle cross section of the SEM image, was averaging process performed in the pixel range of 3×3 using a commercial image analysis software iTEM (TEM camera control, image analysis software, EMSIS GmbH); and contrast optimization was performed by a process of highlighting the edge part. Then, a binarization process, and a process of removing noises and highlighting particles with low contrast by image processing were performed; and a second averaging process in the pixel range of 3×3, and a process of highlighting the edge part were performed. FIG. 6-2 shows an image in which the particle cross section was divided into four regions (Region 1 to Region 4) on the image latitudinally every 90° around the center point of the maximum diameter as a center.

The variation coefficient of the area ratios: (s/A)×100(%), wherein A is an area of a respective divided region, and s is a sum of cross section areas of the main agent included in the respective divided region, in the FIB cross section of curcumin particles of FIG. 6-2, was 0.162.

Example 2

A suspension containing microspheres was prepared in the same manner as in Example 1 except that polylactic acid (Resomer R202H, Evonik AG) was used instead of lactic acid-glycolic acid copolymer (Resomer RG752H, Evonik AG). The average volume-based particle diameter of the obtained microspheres was 7.3 μm. Representative particles were frozen with liquid nitrogen, and an FIB cross section was prepared, and an SEM image was observed.

The observed SEM image was image analyzed in the same manner as in Example 1. The variation coefficient of the area ratios: (s/A)×100(%), wherein A is an area of a respective divided region, and s is a sum of cross section areas of the main agent included in the respective divided region, was 0.215.

Example 3

Dichloromethane (Kanto Chemical Co., Inc.) was added to lactic acid-glycolic acid copolymer (Resomer RG504, Evonik AG) and progesterone (Sigma-Aldrich Co., LLC) as a main agent, so that the concentration of lactic acid-glycolic acid copolymer was 13% by mass, and the concentration of progesterone was 1.0% by mass. Lactic acid-glycolic acid copolymer and progesterone were dissolved using a high-speed rotatory dispersing apparatus Clearmix Dissolver (M. Technique Co., Ltd.) to obtain a solution of PLGA and the main agent. Thereafter, the solution was filtrated with a 0.2 μm air vent filter (φ 62 mm, Merck KGaA). An aqueous PVA solution was prepared in the same manner as in Reference Example 1. The aqueous PVA solution was added in a tank for collecting emulsified particles of PLGA and the main agent beforehand, and was slowly stirred to an extent that the solution surface just moved.

<Preparation of Microsphere>

As the step of forming particles, the prepared solution of PLGA and the main agent and the aqueous PVA solution were mixed using the pulverizing apparatus described in JP 2011-189348 in the same manner as in Reference Example 1. Specifically, the prepared aqueous PVA solution was introduced from the first introduction path d1 into the space between the processing surfaces 1 and 2 at 0.01 MPaG, at 50 mL/min and at 30° C., and the prepared solution of PLGA and the main agent was introduced from the second introduction path d2 into the space between the processing surfaces 1 and 2 at 0.35 MPaG, at 16 mL/min of 30° C. at the rotational speed of the processing member 10 of 1,700 rpm, and the aqueous PVA solution and the solution of PLGA and the main agent were mixed in a forced thin film to prepare emulsified particles of PLGA and the main agent containing dichloromethane in the space between the processing surfaces 1 and 2. The fluid containing the emulsified particles of PLGA and the main agent (hereinafter, emulsified particle dispersion of PLGA and the main agent) in the space between the processing surfaces 1 and 2 was discharged from the space between the processing surfaces 1 and 2 of the pulverizing apparatus. The emulsified particle dispersion of PLGA and the main agent was collected in a recovery tank keeping the pressure of 0.02 MPaG.

The step of removing a solvent was performed in the same manner as in Examples 1 and 2. The average volume-based particle diameter of the obtained microspheres was 34.8 μm. Representative particles were frozen with liquid nitrogen, and an FIB cross section was prepared, and an SEM image (FIG. 7-1) was observed.

Figures 1, 7:
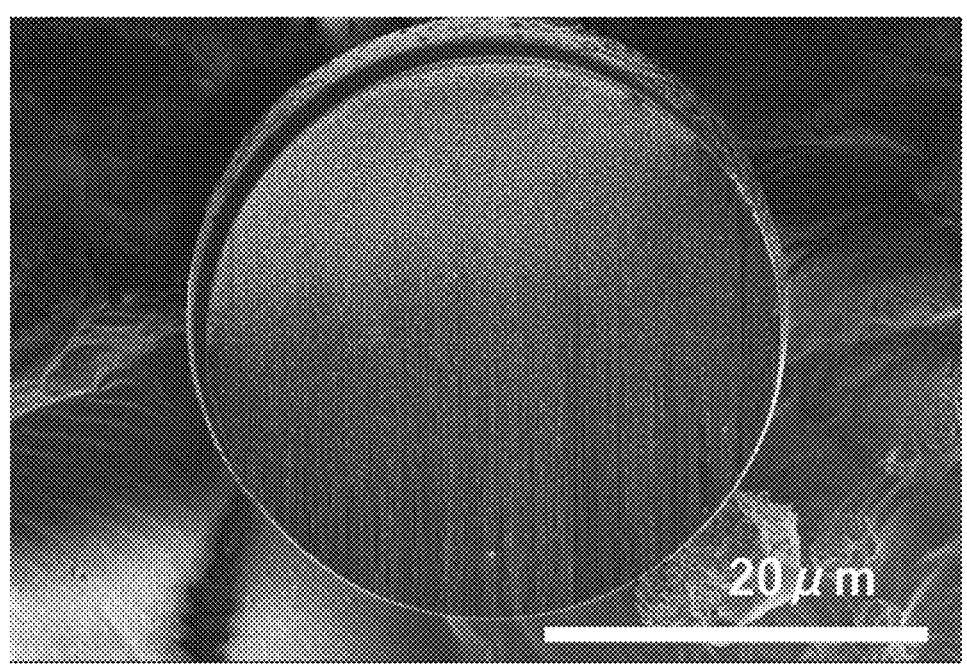
Figures 2, 7:

The observed SEM image was image analyzed in the same manner as in Examples 1 and 2. FIG. 7-2 shows an image prepared by enlarging the SEM image and a binarization process. The variation coefficient of the area ratios: (s/A)×100(%), wherein A is an area of a respective region obtained by dividing into four regions on the SEM image latitudinally every 90° around the center point of the maximum diameter as a center, and s is a sum of cross section areas of the main agent included in the respective divided region, was 0.054.

Example 4

Dichloromethane (Kanto Chemical Co., Inc.) was added to lactic acid-glycolic acid copolymer (Resomer RG504, Evonik AG) and probcol (FUJIFILM Wako Pure Chemical Corporation, for cell biochemistry) as a main agent, so that the concentration of lactic acid-glycolic acid copolymer was 13% by mass, and the concentration of probcol was 1.0% by mass. Lactic acid-glycolic acid copolymer and probcol were dissolved using a high-speed rotatory dispersing apparatus Clearmix Dissolver (M. Technique Co., Ltd.) to obtain a solution of PLGA and the main agent. Thereafter, the solution was filtrated with a 0.2 μm air vent filter (φ 62, Merck KGaA). An aqueous PVA solution was prepared in the same manner as in Reference Example 1. The aqueous PVA solution was added in a tank for collecting emulsified particles of PLGA and the main agent beforehand, and was slowly stirred to an extent that the solution surface just moved.

The step of removing a solvent was performed in the same manner as in Examples 1 to 3. The average volume-based particle diameter of the obtained microspheres was 32.5 μm. Representative particles were frozen with liquid nitrogen, and an FIB cross section was prepared, and an SEM image (FIG. 8-1) was observed.

Figures 1, 8:
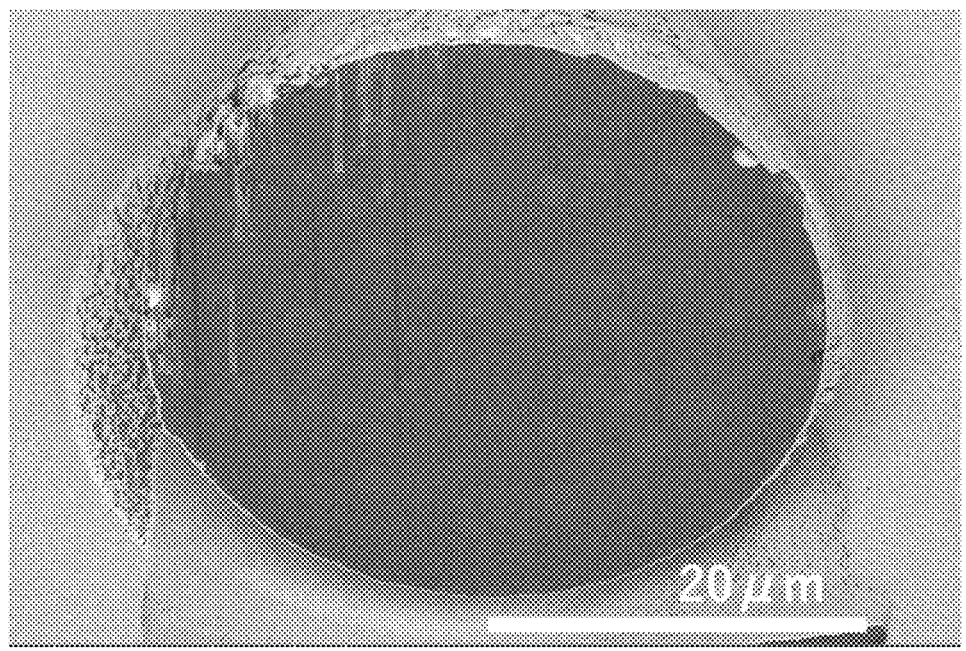
Figures 2, 8:
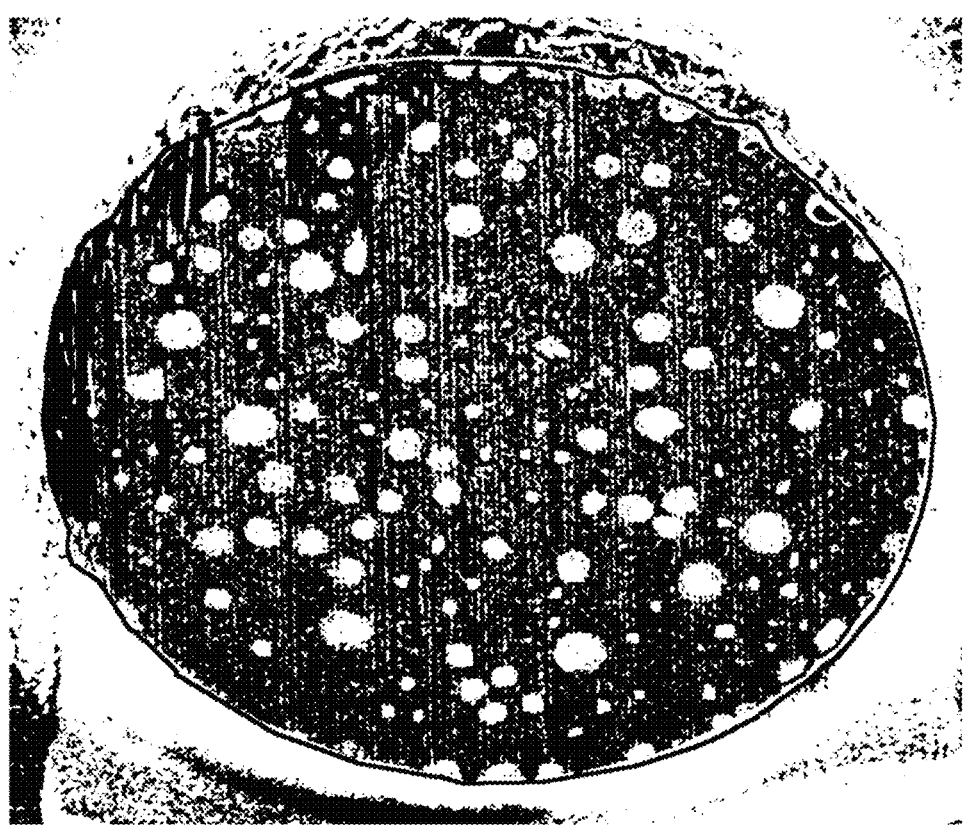

The observed SEM image was image analyzed in the same manner as in Examples 1 to 3. FIG. 8-2 shows an image prepared by a binarization process. The variation coefficient of the area ratios: (s/A)×100(%), wherein A is an area of a respective region obtained by dividing into four regions on the SEM image latitudinally every 90° around the center point of the maximum diameter as a center, and s is a sum of cross section areas of the main agent included in the respective divided region, was 0.244.

Example 5

<Preparation of Solution of PLC and Main Agent and Aqueous PVA Solution>

96.0% by mass of ethyl acetate (Kanto Chemical Co., Inc.) was added to polycaprolactone (PCL, Resomer C209, Evonik AG) and ivermectin (Sigma-Aldrich Co., LLC) as a main agent, so that the concentration of PCL was 3.6% by mass, and the concentration of ivermectin was 0.4% by mass. PCL and ivermectin were dissolved using a high-speed rotatory dispersing apparatus Clearmix Dissolver (M. Technique Co., Ltd.) to obtain a solution of PCL and the main agent. Thereafter, the solution was filtrated with a 0.2 μm air vent filter (φ 62 mm, Merck KGaA). An aqueous PVA solution was prepared in the same manner as in Reference Example 1. The aqueous PVA solution was added in a tank for collecting emulsified particles of PCL and the main agent beforehand, and was slowly stirred to an extent that the solution surface just moved.

<Preparation of Microsphere>

As the step of forming particles, the prepared solution of PCL and the main agent and the aqueous PVA solution were mixed using the pulverizing apparatus described in JP 2011-189348 in the same manner as in Reference Example 1. Specifically, the prepared aqueous PVA solution was introduced from the first introduction path d1 into the space between the processing surfaces 1 and 2 at 0.05 MPaG, at 50 mL/min and at 25° C., and the prepared solution of PCL and the main agent was introduced from the second introduction path d2 into the space between the processing surfaces 1 and 2 at 0.1 MPaG, at 16 mL/min of 25° C. at the rotational speed of the processing member 10 of 3,000 rpm, and the aqueous PVA solution and the solution of PCL and the main agent were mixed in a forced thin film to prepare emulsified particles of PCL and the main agent containing ethyl acetate in the space between the processing surfaces 1 and 2. The fluid containing the emulsified particles of PCL and the main agent (hereinafter, emulsified particle dispersion of PCL and the main agent) in the space between the processing surfaces 1 and 2 was discharged from the space between the processing surfaces 1 and 2 of the pulverizing apparatus. The emulsified particle dispersion of PCL and the main agent was collected in a recovery tank keeping the pressure of 0.03 MPaG.

The step of removing a solvent was performed for 5 hours in the same manner as in Examples 1 to 4. The average volume-based particle diameter of the obtained microspheres was 12.9 μm. Representative particles were frozen with liquid nitrogen, and an FIB cross section was prepared, and an SEM image was observed.

The observed SEM image was image analyzed in the same manner as in Example 1. The variation coefficient of the area ratios: (s/A)×100(%), wherein A is an area of a respective region obtained by dividing into four regions on the SEM image, and s is a sum of cross section areas of the main agent included in the respective divided region, was 0.067.

Example 6

A suspension containing microspheres was prepared in the same manner as in Example 5 except that orbifloxacin (FUJIFILM Wako Pure Chemical Corporation) was used instead of ivermectin. The average volume-based particle diameter of the obtained microspheres was 13.5 μm. Representative particles were frozen with liquid nitrogen, and an FIB cross section was prepared, and an SEM image was observed.

The observed SEM image was image analyzed in the same manner as in Example 1. The variation coefficient of the area ratios: (s/A)×100(%), wherein A is an area of a respective region obtained by dividing into four regions on the SEM image, and s is a sum of cross section areas of the main agent included in the respective divided region, was 0.070.

Example 7

<Preparation of Solution of Ethyl Cellulose and Main Agent and Aqueous PVA Solution>

98.67% by mass of methyl acetate (Kanto Chemical Co., Inc.) was added to ethyl cellulose (FUJIFILM Wako Pure Chemical Corporation) and raspberry ketone (FUJIFILM Wako Pure Chemical Corporation) as a main agent, so that the concentration of ethyl cellulose was 1.0% by mass, and the concentration of raspberry ketone was 0.33% by mass. Ethyl cellulose and raspberry ketone were dissolved using a high-speed rotatory dispersing apparatus Clearmix Dissolver (M. Technique Co., Ltd.) to obtain a solution of ethyl cellulose and the main agent. Thereafter, the solution was filtrated with a 0.2 μm air vent filter (φ 62 mm, Merck KGaA). Ion exchanged water was added to polyvinyl alcohol (PVA, EG-40P, Nippon Synthetic Chemical Industry Co., Ltd.) so that the concentration was 1.5% by mass, and polyvinyl alcohol was dissolved using a high-speed rotatory dispersing apparatus Clearmix (M. Technique Co., Ltd.) to obtain an aqueous PVA solution. Methyl acetate was added to the PVA solution so that the concentration was 23.5% by mass, and methyl acetate was dissolved using a high-speed rotatory dispersing apparatus Clearmix (M. Technique Co., Ltd.) to obtain a mixed solution of PVA, water and methyl acetate. Thereafter, the solution was filtrated with a hydrophilic PVDF membrane filter (φ 47 mm, Merck KGaA).

<Preparation of Microsphere>

As the step of forming particles, the prepared solution of ethyl cellulose and the main agent and the aqueous PVA solution were mixed using the pulverizing apparatus described in JP 2011-189348 in the same manner as in Reference Example 1. Specifically, the prepared aqueous PVA solution was introduced from the first introduction path d1 into the space between the processing surfaces 1 and 2 at 0.1 MPaG or less, at 50 mL/min and at 25° C., and the prepared solution of ethyl cellulose and the main agent was introduced from the second introduction path d2 into the space between the processing surfaces 1 and 2 at 0.1 MPaG, at 16 mL/min of 25° C. at the rotational speed of the processing member 10 of 500 rpm, and the aqueous PVA solution and the solution of ethyl cellulose and the main agent were mixed in a forced thin film to prepare emulsified particles of ethyl cellulose and the main agent containing methyl acetate in the space between the processing surfaces 1 and 2. The fluid containing the emulsified particles of ethyl cellulose and the main agent (hereinafter, emulsified particle dispersion of ethyl cellulose and the main agent) in the space between the processing surfaces 1 and 2 was discharged from the space between the processing surfaces 1 and 2 of the pulverizing apparatus. The emulsified particle dispersion of ethyl cellulose and the main agent was collected in a recovery tank.

Figure 9:
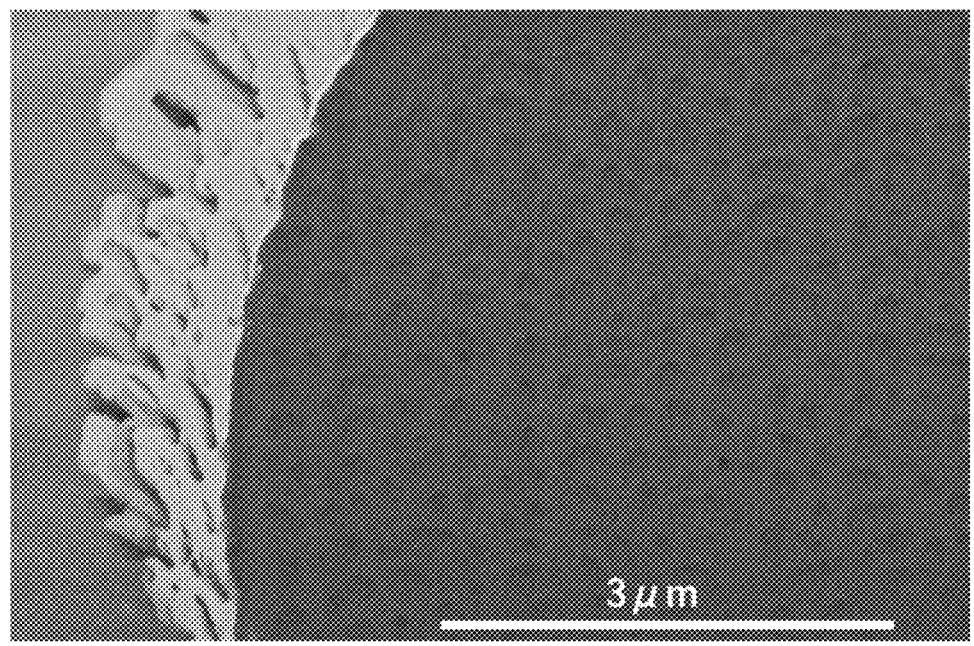
FIG. 9 shows an SEM image prepared by enlarging a cross section of the microsphere of Example 7.

Next, as the step of removing a solvent, ion exchanged water was added in 1.5 times the amount of the discharged liquid at a rate of 1 mL/min, to solidify the surface of the particles. Then, methyl acetate was removed under a reduced pressure of −0.08 MPaG using a rotary evaporator to obtain a suspension containing microspheres (microsphere suspension). The average volume-based particle diameter of the obtained microspheres was 10.7 μm. Representative particles were frozen with liquid nitrogen, and an FIB cross section was prepared, and an SEM image was observed. FIG. 9 shows an enlarged photograph of the SEM cross section.

The observed SEM image was image analyzed in the same manner as in Examples 1 to 6. The variation coefficient of the area ratios: (s/A)×100(%), wherein A is an area of a respective region obtained by dividing into four regions on the SEM image latitudinally every 90° around the center point of the maximum diameter as a center, and s is a sum of cross section areas of the main agent included in the respective divided region, was 0.245.

Example 8

A suspension containing microspheres was prepared in the same manner as in Example 7 except that cellulose acetate (Kanto Chemical Co., Inc.) was used instead of ethyl cellulose. The average volume-based particle diameter of the obtained microspheres was 11.2 µm. Representative particles were frozen with liquid nitrogen, and an FIB cross section was prepared, and an SEM image was observed.

Figure 10:
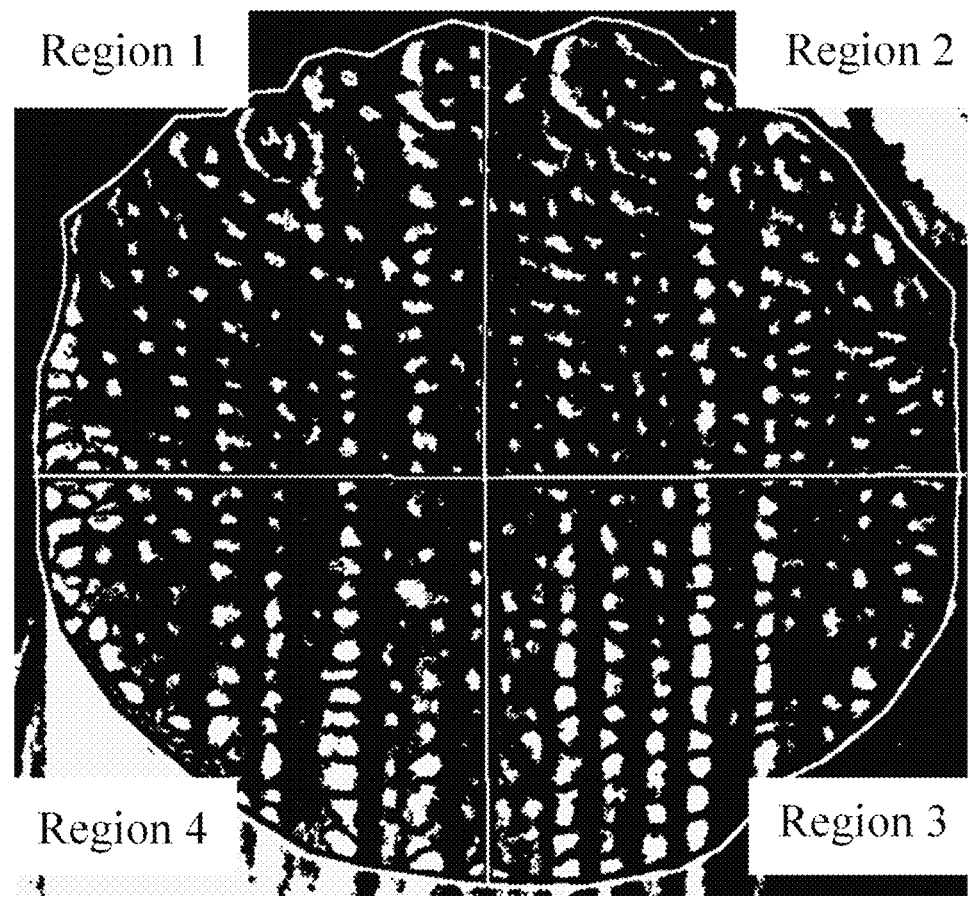
FIG. 10 shows an image prepared by dividing the SEM image of a cross section of the microsphere of Example 8 into four regions and a binarization process, for calculating area ratios: (s/A)×100(%), wherein A is an area of a respective divided region, and s is a sum of cross section areas of the main agent included in the respective divided region.

The observed SEM image was image analyzed in the same manner as in Example 1. FIG. 10 shows an SEM cross section after a binarization process. The variation coefficient of the area ratios: (s/A)×100(%), wherein A is an area of a respective region obtained by dividing into four regions on the SEM image latitudinally every 90° around the center point of the maximum diameter as a center, and s is a sum of cross section areas of the main agent included in the respective divided region, was 0.317.

Comparative Example 1

A dispersion containing emulsified particles of PLGA and the main agent was prepared by performing the step of forming particles under the same conditions as in Example 4. Next, as the step of removing a solvent, dichloromethane was removed in the atmosphere from the collected discharged fluid over 42 hours, while stirring the discharged fluid at a peripheral speed of 4.7 m/sec using Clearmix Dissolver (M. Technique Co., Ltd.), to obtain a suspension containing microspheres (microsphere suspension). The average volume-based particle diameter of the obtained microspheres was 31.8 µm. Representative particles were frozen with liquid nitrogen, and an FIB cross section was prepared, and an SEM image was observed.

Figure 11:
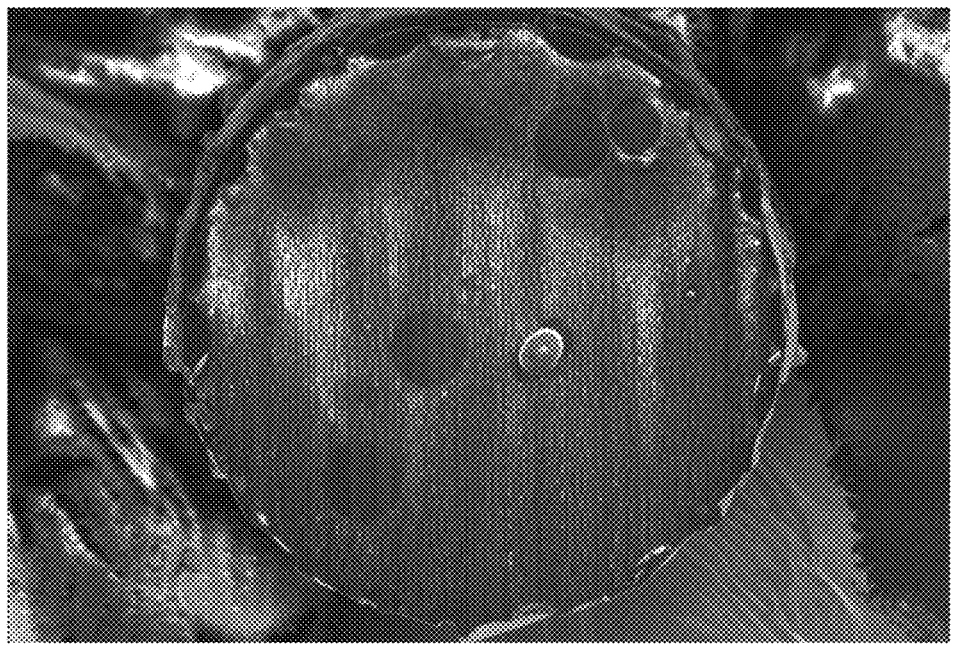
FIG. 11 shows an SEM image of a cross section of the microsphere of Comparative Example 1.

The observed SEM image (FIG. 11) was image analyzed in the same manner as in Examples 1 to 3. The variation coefficient of the area ratios: (s/A)×100(%), wherein A is an area of a respective region obtained by dividing into four regions on the SEM image concentrically by dividing the radius into four equal parts from the center point of the maximum diameter of an image prepared by a binarization process, and s is a sum of cross section areas of the main agent included in the respective divided region, was 0.482.

Comparative Example 2

Figure 12:
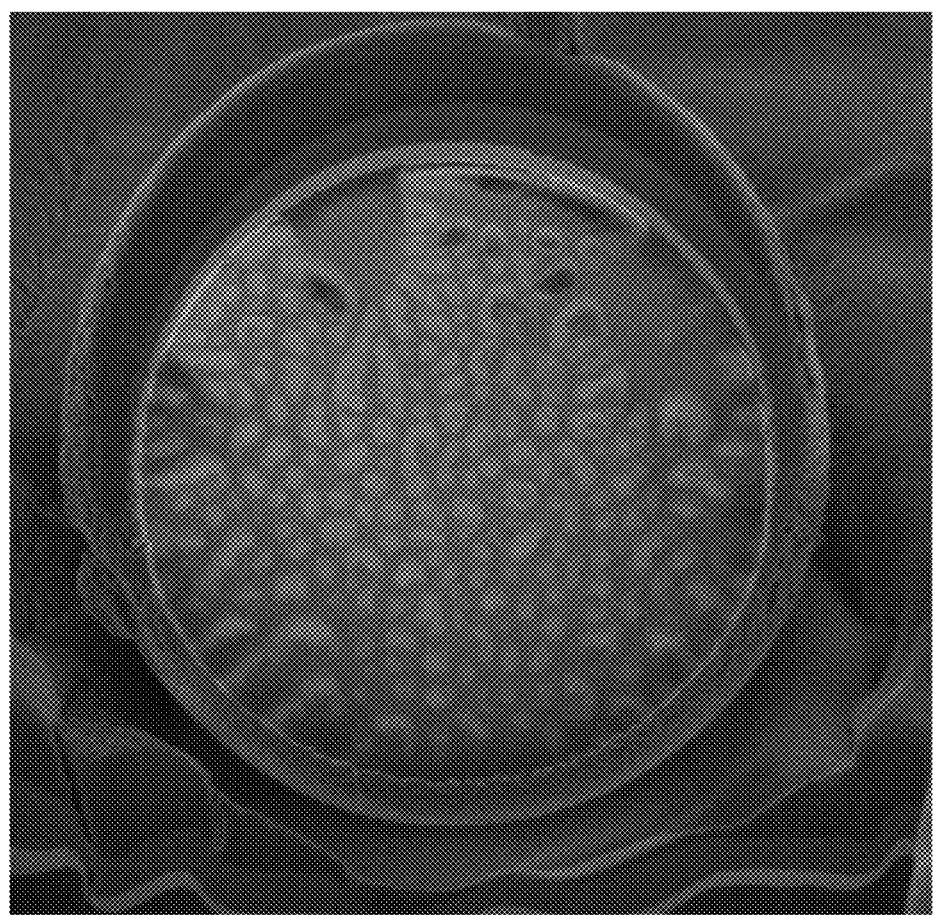
FIG. 12 shows an SEM image of a cross section of the microsphere of Comparative Example 2.

A dispersion containing microspheres was prepared with the same formulation as in Example 4, by performing the step of forming particles and the step of removing a solvent under the same conditions as in Example 4, except that dissolution of PLGA and the medicine was performed by stirring for 10 minutes with a propeller type stirring apparatus (Three-One Motor). The average volume-based particle diameter of the obtained microspheres was 29.8 µm. Representative particles were frozen with liquid nitrogen, and an FIB cross section was prepared, and an SEM image (FIG. 12) was observed.

The observed SEM image was image analyzed in the same manner as in Examples 1 to 4. The variation coefficient of the area ratios: (s/A)×100(%), wherein A is an area of a respective region obtained by dividing into four regions in the vertical direction on the SEM image, and s is a sum of cross section areas of the main agent included in the respective divided region, was 0.452.

Comparative Example 3

69.75% by mass of dichloromethane (Kanto Chemical Co., Inc.) and 25% by mass of acetone (Kanto Chemical Co., Inc.) were added to lactic acid-glycolic acid copolymer (Resomer RG504, Evonik AG) and curcumin (FUJIFILM Wako Pure Chemical Corporation, Wako special grade) as a main agent, so that the concentration of lactic acid-glycolic acid copolymer was 5.0% by mass, and the concentration of curcumin was 0.25% by mass. Lactic acid-glycolic acid copolymer and curcumin were dissolved using a high-speed rotatory dispersing apparatus Clearmix Dissolver (M. Technique Co., Ltd.) to obtain a solution of PLGA and the main agent. Thereafter, the solution was filtrated with a 0.2 µm air vent filter (φ 62, Merck KGaA). An aqueous PVA solution was prepared in the same manner as in Reference Example 1. The aqueous PVA solution was added in a tank for collecting emulsified particles of PLGA and the main agent beforehand, and was slowly stirred to an extent that the solution surface just moved.

Figure 13:
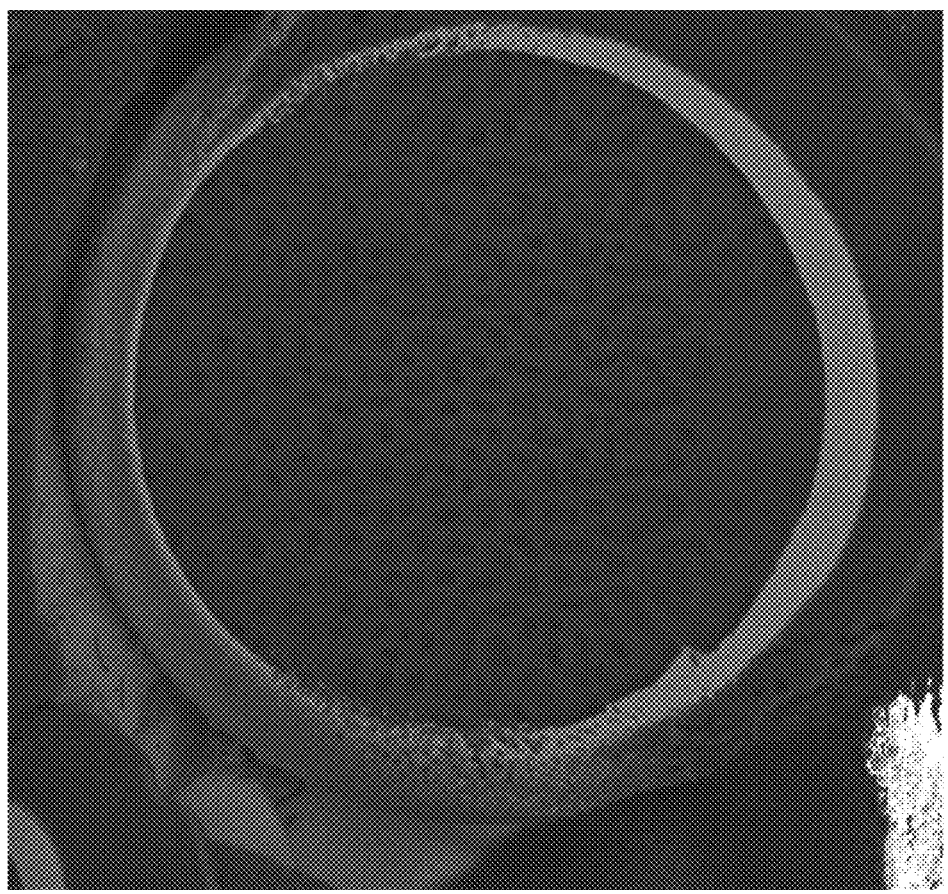
FIG. 13 shows an SEM image of a cross section of the microsphere of Comparative Example 3.

A dispersion containing microspheres was prepared by performing the step of forming particles and the step of removing a solvent under the same conditions as in Example 1. The average volume-based particle diameter of the obtained microspheres was 6.8 µm. Representative particles were frozen with liquid nitrogen, and an FIB cross section was prepared, and an SEM image (FIG. 13) was observed.

The observed SEM image was image analyzed in the same manner as in Examples 1 to 4. The variation coefficient of the area ratios: (s/A)×100(%), wherein A is an area of a respective region obtained by dividing into four regions in the vertical direction on the SEM image, and s is a sum of cross section areas of the main agent included in the respective divided region, was 0.422.

Comparative Example 4

69.5% by mass of dichloromethane (Kanto Chemical Co., Inc.) and 25% by mass of acetone (Kanto Chemical Co., Inc.) were added to lactic acid-glycolic acid copolymer (Resomer RG504, Evonik AG) and progesterone (Sigma-Aldrich Co., LLC) as a main agent, so that the concentration of lactic acid-glycolic acid copolymer was 5.0% by mass, and the concentration of curcumin was 0.3% by mass. Lactic acid-glycolic acid copolymer and progesterone were dissolved using a high-speed rotatory dispersing apparatus Clearmix Dissolver (M. Technique Co., Ltd.) to obtain a solution of PLGA and the main agent. Thereafter, the solution was filtrated with a 0.2 µm air vent filter (φ 62, Merck KGaA). An aqueous PVA solution was prepared in the same manner as in Reference Example 1. The aqueous PVA solution was added in a tank for collecting emulsified particles of PLGA and the main agent beforehand, and was slowly stirred to an extent that the solution surface just moved.

Figure 14:
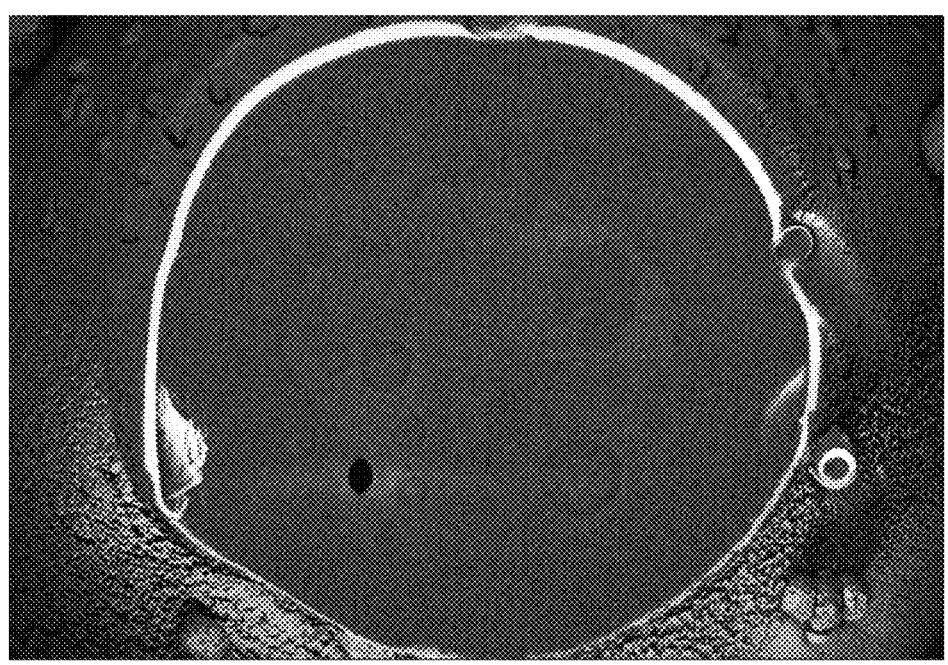
FIG. 14 shows an SEM image of a cross section of the microsphere of Comparative Example 4.

A dispersion containing microspheres was prepared by performing the step of forming particles and the step of removing a solvent under the same conditions as in Example 3. The average volume-based particle diameter of the obtained microspheres was 21.6 µm. Representative particles were frozen with liquid nitrogen, and an FIB cross section was prepared, and an SEM image (FIG. 14) was observed.

The observed SEM image was image analyzed in the same manner as in Examples 1 to 4. The variation coefficient of the area ratios: (s/A)×100(%), wherein A is an area of a respective region obtained by dividing into four regions in the vertical direction on the SEM image, and s is a sum of cross section areas of the main agent included in the respective divided region, was 1.049.

Comparative Example 5

A dispersion containing microspheres was prepared in the same manner as in Example 5, except that the concentration of ivermectin in the solution of PCL and the main agent was changed from 0.4% by mass to 4% by mass. The average volume-based particle diameter of the obtained microspheres was 11.8 µm. Representative particles were frozen with liquid nitrogen, and an FIB cross section was prepared, and an SEM image was observed.

The observed SEM image was image analyzed in the same manner as in Example 1. The variation coefficient of the area ratios: (s/A)×100(%), wherein A is an area of a respective region obtained by dividing into four regions on the SEM image, and s is a sum of cross section areas of the main agent included in the respective divided region, was 0.361.

Apart of the conditions of Examples 1 to 8, Comparative Examples 1 to 5, and Reference Example 1 (containing only PLGA) is shown in Tables 1 and 2.

TABLE 1

|  | Example 1 | Example 2 | Example 3 | Example 4 | Example 5 | Example 6 | Example 7 | Example 8 |
|---|---|---|---|---|---|---|---|---|
| Main agent (Medicine) | Curcumin | Curcumin | Progesterone | Probucol | Ivermectin | Orbifloxacin | raspberry ketone | raspberry ketone |
| Concentration of medicine | 0.5% by mass | 0.5% by mass | 1% by mass | 1% by mass | 0.4% by mass | 0.4% by mass | 0.33% by mass | 0.33% by mass |
| Polymer | PLGA (RG752H) | PLA (R202H) | PLGA (RG504) | PLGA (RG504) | PCL (C209) | PCL (C209) | ethyl cellulose | Cellulose acetate |
| Concentration of polymer | 10% by mass | 10% by mass | 13% by mass | 13% by mass | 3.6% by mass | 3.6% by mass | 1% by mass | 1% by mass |
| Poor solvent | 1.5% by mass aq. PVA solution | 1.5% aq. PVA solution | 1.5% by mass aq. PVA solution | 1.5% by mass aq. PVA solution | 1.5% by mass aq. PVA solution | 1.5% by mass aq. PVA solution | 76.5% by mass (1.5% by mass aq. PVA solution) 23.5% by mass (methyl acetate) | 76.5% by mass (1.5% by mass aq. PVA solution) 23.5% by mass (methyl acetate) |
| Drying condition | Argon flow 3.5 hours | Argon flow 3.5 hours | Argon flow 3.5 hours | Argon flow 3.5 hours | Argon flow 5 hours | Argon flow 5 hours | water dropping 1 mL/min (1.5 times amount of discharged liquid) removal under reduced pressure using evaporator | water dropping 1 mL/min (1.5 times amount of discharged liquid) removal under reduced pressure using evaporator |
| Preparation condition of solution of polymer and main agent | High speed stirring | High speed stirring | High speed stirring | High speed stirring | High speed stirring | High speed stirring | High speed stirring | High speed stirring |
| Particle diameter of microsphere | 7.5 µm | 7.3 µm | 34.8 µm | 32.5 µm | 12.9 µm | 13.5 µm | 10.7 µm | 11.2 µm |

TABLE 2

|  | Comparative Example 1 | Comparative Example 2 | Comparative Example 3 | Comparative Example 4 | Comparative Example 5 | Reference Example 1 |
|---|---|---|---|---|---|---|
| Main agent (Medicine) | Probucol | Probucol | Curcumin | Progesterone | Ivermectin | — |
| Concentration of medicine | 1% by mass | 1% by mass | 0.25% by mass | 0.3% by mass | 4% by mass | — |
| Polymer | PLGA (RG504) | PLGA (RG504) | PLGA (RG504) | PLGA (RG504) | PCL (C209) | PLGA (RG504) |
| Concentration of polymer | 13% by mass | 13% by mass | 5% by mass | 5% by mass | 3.6% by mass | 13% by mass |
| Poor solvent | 1.5% by mass aq. PVA solution | 1.5% by mass aq. PVA solution | 1.5% by mass aq. PVA solution | 1.5% by mass aq. PVA solution | 1.5% by mass aq. PVA solution | 1.5% by mass aq. PVA solution |
| Drying condition | In atmosphere 42 hours | Argon flow 3.5 hours | Argon flow 3.5 hours | Argon flow 3.5 hours | Argon flow 5 hours | Argon flow 3.5 hours |
| Preparation condition of solution of polymer and main agent | High speed stirring | Propeller | High speed stirring | High speed stirring | High speed stirring | High speed stirring |

TABLE 2-continued

|  | Comparative Example 1 | Comparative Example 2 | Comparative Example 3 | Comparative Example 4 | Comparative Example 5 | Reference Example 1 |
|---|---|---|---|---|---|---|
| Particle diameter of micro sphere | 31.8 μm | 29.8 μm | 6.8 μm | 21.6 μm | 11.8 μm | 34.0 μm |

Area ratios (%) in respective regions, standard deviations, averages and variation coefficients (CV values) of a microsphere having a representative particle diameter of Examples 1 to 8, Comparative Examples 1 to 5, and leuplin (registered trademark) for injection 1.88 mg are shown in Table 3.

TABLE 3

| | Area ratio (%) | | | | | | | |
|---|---|---|---|---|---|---|---|---|
| | Region 1 | Region 2 | Region 3 | Region 4 | Difference maximum − minimum | Standard deviation | Average | CV value |
| Example 1 | 44.36 | 43.49 | 34.32 | 32.12 | 9.16 | 6.26 | 38.57 | 0.162 |
| Example 2 | 31.76 | 48.32 | 31.02 | 39.82 | 16.56 | 8.11 | 37.73 | 0.215 |
| Example 3 | 34.78 | 37.25 | 34.32 | 38.39 | 4.07 | 1.95 | 36.19 | 0.054 |
| Example 4 | 29.28 | 34.78 | 19.98 | 36.06 | 16.08 | 7.31 | 30.03 | 0.244 |
| Example 5 | 22.53 | 23.42 | 20.15 | 23.16 | 3.27 | 1.49 | 22.32 | 0.067 |
| Example 6 | 13.58 | 12.56 | 11.53 | 12.11 | 2.05 | 0.87 | 12.45 | 0.070 |
| Example 7 | 15.68 | 11.56 | 17.21 | 10.12 | 7.09 | 3.35 | 13.64 | 0.245 |
| Example 8 | 10.16 | 9.51 | 16.80 | 17.64 | 8.12 | 4.28 | 13.53 | 0.317 |
| Comparative Example 1 | 16.75 | 8.32 | 26.53 | 30.12 | 21.80 | 9.85 | 20.43 | 0.482 |
| Comparative Example 2 | 27.63 | 15.12 | 29.79 | 10.56 | 19.23 | 9.39 | 20.78 | 0.452 |
| Comparative Example 3 | 17.31 | 28.87 | 24.43 | 9.57 | 19.30 | 8.45 | 20.05 | 0.422 |
| Comparative Example 4 | 1.231 | 18.53 | 23.62 | 1.123 | 22.50 | 11.67 | 11.13 | 1.049 |
| Comparative Example 5 | 51.32 | 27.12 | 66.48 | 40.31 | 26.17 | 16.70 | 46.31 | 0.361 |
| Leuplin (Registered trademark) | 22.01 | 8.95 | 1.20 | 2.22 | 20.81 | 9.58 | 8.60 | 1.114 |

As can be seen from Tables 1 to 3, the variation coefficients of area ratios of occupation of the main agent in respective regions in the particles of Examples 1 to 8, were 0.35 or less, and the main agent was uniformly dispersed in the particles, even when any kind of a polymer was used. In Comparative Example 3, when the concentration of PLGA was decreased, uniformity in the particles was lowered, and the variation coefficients of area ratios of occupation of the main agent in respective regions, became bigger to 0.422, even when conditions in the step of forming particles and the step of removing a solvent were the same as those in Example 1.

In Example 4 and Comparative Example 1, the particle diameter of the microparticles of the main agent varied according to difference of the drying conditions and drying time. In Comparative Example 1 in which the drying time was long, uniformity of the main agent in the microsphere particles was lowered, and the variation coefficient of area ratios of occupation of the main agent in respective regions, became bigger to 0.482. In Comparative Examples 3 and 4 in which the concentrations of PLGA and the medicine were decreased compared with those in Examples, percentage of contraction during drying became bigger, and the main agent was biased in the particles, and the variation coefficients of area ratios of occupation of the main agent in respective regions, exceeded 0.35. In Comparative Example 5 in which the concentration of the main agent was increased compared with those in Example 5, uniformity of the main agent in the microsphere particles was lowered, and the variation coefficient of area ratios of occupation of the main agent in respective regions, became bigger to 0.361.

INDUSTRIAL APPLICABILITY

The present invention provides a microsphere capable of appropriately controlling the initial release amount of a main agent and its release rate during a subsequent release period, and continuously releasing the main agent in vivo for a predetermined period of time.

The invention claimed is:

1. A microsphere in which a main agent is uniformly dispersed in a polymer matrix,
    wherein an average volume-based particle diameter of the microsphere is 1 μm or more and 150 μm or less, and a variation coefficient of area ratios in four regions is 0.25 or less, wherein the area ratios in four regions are calculated by $(s/A) \times 100$ (%) wherein the four regions are prepared by preparing a cross section observation sample obtained by cutting the microsphere; observing the cross section observation sample with an electron microscope at a magnification capable of confirming the main agent in the microsphere or a higher magnification; and dividing the electron microscope observation image into four regions; and A is an area of a respective divided region, and s is a sum of cross section areas of the main agent included in the respective divided region, the polymer matrix is composed of at least one polymer selected from the group consisting of poly (lactide-co-glycolide) (PLGA), polylactide (PLA), polycaprolactone (PCL) and ethyl cellulose (EC), the main agent is a pharmaceutical compound, a functional food compound, a functional cosmetic compound, an animal administration compound, or an agricultural compound, which is lipophilic, a content of the main agent in the microsphere is 0.10 to 50% by mass relative to the total amount of the microsphere, and the microsphere is produced by continuously feeding to a pulverizing apparatus a solution containing the at least one polymer and the main agent obtained by dissolving or dispersing the at least one polymer and the main agent in a good solvent of the at least one polymer with high speed stirring, and a solution containing a poor solvent of the at least one polymer to prepare emulsified particles; and removing the good solvent from the produced particles, a content of the at least one polymer is 1 to 30% by mass relative to the total mass of the solution containing the at least one polymer and the main agent, and the removal of the good solvent is performed by flowing a gas, or by using an evaporator under a reduced pressure.

2. The microsphere according to claim 1, wherein an average particle diameter of the dispersed main agent is 5 nm to 500 nm.

3. A sustained release formulation comprising the microsphere according to claim 1.

4. A sustained release formulation comprising the microsphere according to claim 2.

* * * * *